US010682477B2

(12) United States Patent
Gleixner et al.

(10) Patent No.: US 10,682,477 B2
(45) Date of Patent: Jun. 16, 2020

(54) DOSING SYSTEM FOR AN INHALATION DEVICE

(71) Applicant: VECTURA GMBH, Gauting (DE)

(72) Inventors: Raimund Johannes Gleixner, Munich (DE); Monika Hartmann, Kaufering (DE); Martin Christoph Heiss, Appenzell Eggerstanden (CH); Martin Huber, Egenhofen (DE); Tobias Kolb, Neuried (DE); Bernhard Muellinger, Munich (DE)

(73) Assignee: VECTURA GMBH, Gauting (DE)

( * ) Notice: Subject to any disclaimer, the term of this patent is extended or adjusted under 35 U.S.C. 154(b) by 1018 days.

(21) Appl. No.: 14/909,495

(22) PCT Filed: Aug. 18, 2014

(86) PCT No.: PCT/EP2014/067604
§ 371 (c)(1),
(2) Date: Feb. 2, 2016

(87) PCT Pub. No.: WO2015/022436
PCT Pub. Date: Feb. 19, 2015

(65) Prior Publication Data
US 2016/0193434 A1    Jul. 7, 2016

(30) Foreign Application Priority Data

Aug. 16, 2013 (EP) .................................. 13180770

(51) Int. Cl.
*A61M 15/00* (2006.01)
*A61M 11/00* (2006.01)
(Continued)

(52) U.S. Cl.
CPC ...... *A61M 15/0065* (2013.01); *A61M 11/005* (2013.01); *A61M 11/06* (2013.01);
(Continued)

(58) Field of Classification Search
CPC .......... A61M 15/0065; A61M 15/0066; A61M 11/00; A61M 11/005; A61M 11/06;
(Continued)

(56) References Cited

U.S. PATENT DOCUMENTS 4,566,452 A * 1/1986 Farr ...................... A61M 11/002
128/200.18
5,366,122 A * 11/1994 Guentert ............... A61M 13/00
128/200.22
(Continued)

FOREIGN PATENT DOCUMENTS

CN    102198037 A    9/2011
EP    1205199        5/2002
(Continued)

OTHER PUBLICATIONS

European Search Report of European Patent App. No. 13180770.3 dated Jan. 31, 2014.
(Continued)

*Primary Examiner* — Kendra D Carter
*Assistant Examiner* — Jonathan S Paciorek
(74) *Attorney, Agent, or Firm* — Matthew S. Gibson; Ryan P. Cox; Reed Smith LLP

(57) ABSTRACT

The invention relates to a dosing system for an inhalation device which is capable of aliquoting a precise and accurately metered volume from a larger pre-defined fill volume. The dosing system comprises a filling chamber for receiving a liquid to be aerosolized, the filling chamber having a lateral wall, an inlet opening and an outlet opening with a closing means (11) for closing the outlet opening. The dosing system further comprises an overflow chamber surrounding the inlet opening of the filling chamber and a plunger which can be inserted, at least partially, into the filling chamber, and which sealingly contacts the lateral wall (Continued)

such as to displace liquid from said filling chamber upon insertion, and push a metered volume of the liquid out from the filling chamber through the outlet opening and feed it to the nebulizing means of the inhalation device.

10 Claims, 16 Drawing Sheets

(51) Int. Cl.
*A61M 11/06* (2006.01)
*A61M 39/24* (2006.01)

(52) U.S. Cl.
CPC ....... *A61M 39/24* (2013.01); *A61M 2039/248* (2013.01); *A61M 2039/2426* (2013.01)

(58) Field of Classification Search
CPC .. A61M 15/0085; A61M 39/24; A61M 15/02; A61M 2039/2426; A61M 2039/248; A61M 2205/3386; A61M 2205/584
See application file for complete search history.

(56) References Cited

U.S. PATENT DOCUMENTS 8,276,587 B2 10/2012 Zhang
2002/0148465 A1 10/2002 Sealfon
2003/0146300 A1* 8/2003 Denyer .................. A61M 11/00 239/338
2004/0045547 A1* 3/2004 Yamamoto ........ A61M 15/0085 128/200.14
2012/0216800 A1 8/2012 Dyche et al.
2012/0266870 A1 10/2012 Denyer et al.

FOREIGN PATENT DOCUMENTS

EP 1465692 11/2006
GB 2272389 5/1994
JP 2004523294 8/2004
WO 2002074443 9/2002
WO 2002087762 11/2002
WO 2009092650 A1 7/2009
WO 2011089485 7/2011
WO 2012114230 8/2012
WO 2013098334 7/2013

OTHER PUBLICATIONS

The International Preliminary Report on Patentability for PCT/EP14/67604 dated Nov. 18, 2015.
The International Search Report and the Written Opinion for PCT/EP14/67604 dated Nov. 4, 2014.

* cited by examiner

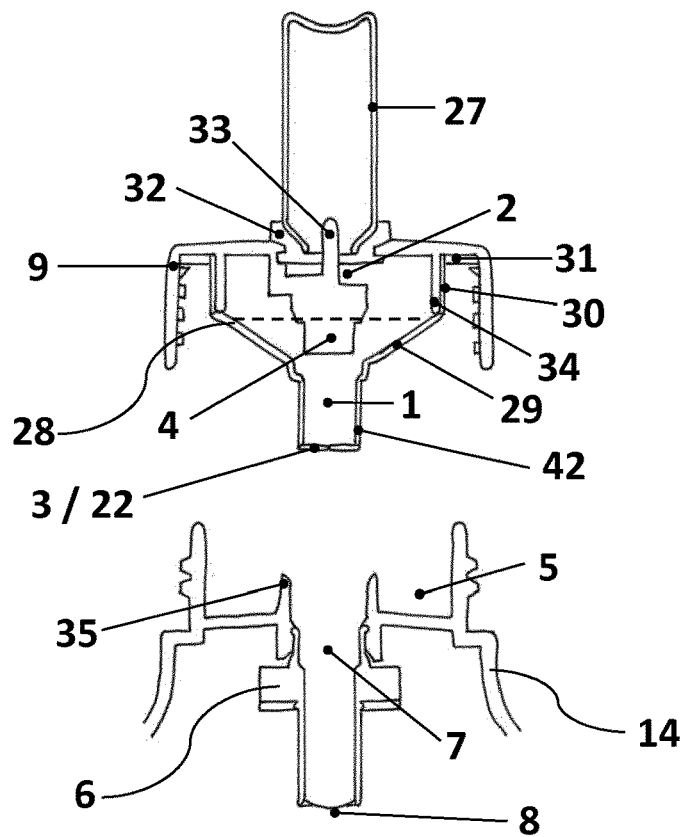
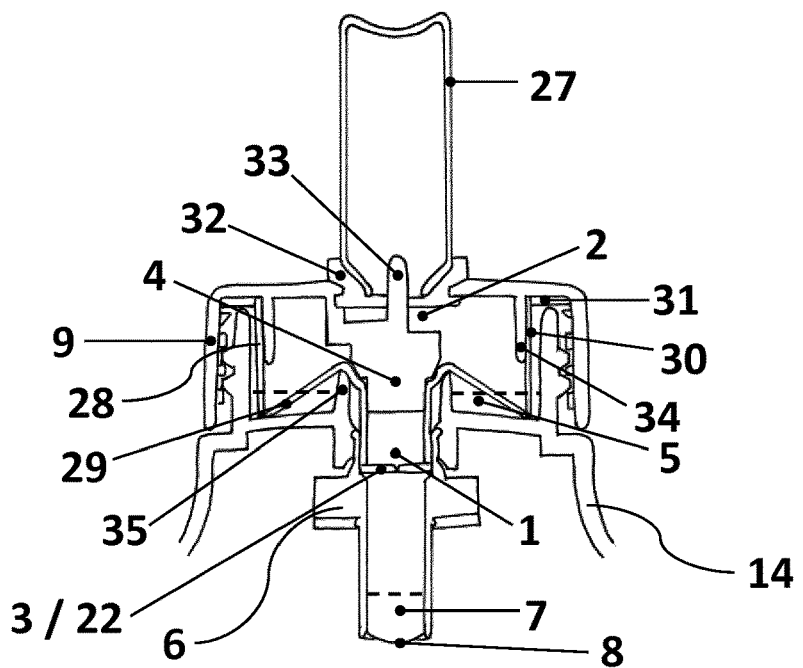
Fig. 10A
Fig. 10B

DOSING SYSTEM FOR AN INHALATION DEVICE

RELATED APPLICATIONS

This application is a United States national stage of International Application No. PCT/EP2014/067604, filed Aug. 18, 2014, which was published as International Publication No. WO 2015/022436 A1, and which claims benefit of European Application No. 13180770.3 filed, Aug. 16, 2013, the entire contents of which are hereby expressly incorporated herein by reference thereto.

BACKGROUND

Inhalation devices are devices capable of delivering aerosols to the body via the lungs. An aerosol is a dispersion of small solid particles or fine liquid droplets in a continuous gas phase. Aerosols of liquid formulations containing a bioactive agent or drug are required for numerous medical applications, such as the inhalative treatment of asthma, cystic fibrosis (CF), and a number of other respiratory diseases. Alternatively, inhalation devices may also be used for the inhalative administration of prophylactic or diagnostic formulations. The inhalation can either be through the mouth (oral inhalation) or through the nose (nasal inhalation); both routes requiring specifically shaped patient interfaces, such as mouthpieces, to reduce aerosol losses to ambient air. More common, especially when targeting the central and/or peripheral airways of the lungs, is oral inhalation.

In some cases, it is desired that the administered aerosol reaches even the smallest branches of the peripheral lungs, such as bronchioles and alveoli to ensure optimal absorption. In order to achieve the desired homogeneous droplet distribution in the gas phase, liquid formulations are typically atomized by the inhalation device. In some cases, the formed droplets may solidify to minute powder particles upon evaporation of the liquid carrier, once the aerosol cloud is expelled from the inhalation device.

Typical inhalation devices include dry powder inhalers (DPI), pressurized metered dose inhalers (pMDI), soft mist inhalers or Rayleigh spray inhalers (such as Respimat® inhaler, Medspray®) and nebulizers (such as ultrasonic nebulizers, jet nebulizers or vibrating mesh nebulizers).

Nebulizes are inhalation devices capable of converting a liquid into an inhalable aerosol in a continuous manner using a nebulizing means (or atomizing means, or aerosol generator), for example a piezo-electrically driven vibrating mesh assembly. Unlike DPIs, pMDIs and soft mist inhalers, which emit metered aerosols only upon actuation and within a very short time frame of few milliseconds, nebulizers operate continuously over the course of a few breaths up to about 45 min (or even longer if the patient requires breaks during an inhalation treatment). During this time, they emit aerosol either constantly or in pulses which are adapted to the user's breathing pattern; e.g., triggered by the onset of inhalation. The duration of the aerosol pulse may also be adapted to the patient's breathing pattern and/or lung function parameters. Nebulizers further differ from the afore mentioned inhalation devices (DPIs, pMDIs and soft mist inhalers) in that they do not per se emit metered amounts of aerosols, because they operate continuously, unless switched off, until the reservoir for the liquid formulation is empty.

An option for dosing the amount of medicine to be inhaled is the use of pre-filled single-use cartridges which are emptied completely into the inhalation device and subsequently nebulized in entirety. While being a favorable approach with regard to dosing reproducibility and hygiene, the dosing flexibility of such pre-filled single-use cartridges is limited.

In cases when the prescribed amount of medicine to be inhaled does not match the volume of the liquid formulation supplied in the container, it would be desirable that the nebulizer is capable of ensuring that only the prescribed amount of liquid is delivered in aerosol form.

A dosing system for such purpose is shown in EP 1 465 692 B1 which discloses a nebulizer including nebulization device and a reservoir which has a metering chamber and a second chamber. The metering chamber defines the volume of the substance to be nebulized and is arranged so as to feed said volume to the nebulization device, while any substance poured into the metering chamber in excess of its volume is received and retained in the second chamber. In other words, the metering chamber is filled until the liquid overflows into the second chamber, and only the metered volume inside the metering chamber is subsequently nebulized. This approach, as depicted as prior art in FIG. 1, is also not very flexible. In addition, dosing reproducibility may be negatively affected e.g. if the user does not keep the device in a horizontal orientation during filling or use. Moreover, any changes in the prescribed dose would require substantial modification of the device and a complete replacement of the metering chamber assembly. Furthermore, the metering system is not suitable for metering very small amounts of liquids which are substantially affected by adhesive and cohesive forces and do not easily flow from one chamber to another.

GB 2 272 389 A discloses another dosing system which is equipped with a manually actuated, syringe-type metering pump comprising a cylinder of defined inner volume and a movable piston. Upon withdrawal of the piston, liquid from a larger liquid supply tank is filled into the cylinder via an inlet valve. When pushing the piston into the cylinder, a droplet of liquid (e.g. 20 µL) is expelled via an outlet valve. An actual metering step occurs only with complete in/out strokes of the piston, making the system inflexible to the dosed volume. Further, due to the manual operation mode the system may fail to provide dosing accuracy and reproducibility.

Further dosing systems are disclosed in EP 1 205 199 A1 and US 2012/0216800 A1. The dosing system shown in both documents comprises a cylindrical filling chamber with a wider top portion and a narrower bottom portion which at its bottom end is closed by a valve. A plunger is inserted into the filling chamber from its wider top end along the chamtier's longitudinal axis. Once the plunger reaches the narrower bottom portion, a seal between plunger and the inner walls of the bottom portion is formed, so that liquid cannot be displaced towards the wider top end anymore. Thus upon continued insertion of the plunger, a metered amount of liquid is pushed out of the filling chamber's bottom portion through the valve, while the excess liquid remains in the filling chamber above the seal. When the plunger is retracted from the bottom portion, this excess liquid can flow into the bottom portion and can also be pushed out through the valve when the plunger is inserted once or several times more.

This can be advantageous in cases, where the filling chamber is deliberately filled with a multi-dose amount of liquid and the dosing system is supposed to be actuated repeatedly. However, it is highly undesirable in cases where such re-dosing is unintended and/or may even be harmful due to overdosing; e.g. when only specific fractions of typically marketed volumes are supposed to be administered to neonates, infants, children or to subjects with an improving health-condition. For instance, a nebulizer solution may only be available in ampoules containing 1 mL or more, while the subject should receive only 200 μL. The above described dosing systems would either allow the unintended administration of an extra 800 μL to a subject, or they would not nebulize all of the intended 200 μL due to adhesion- and cohesion induced losses in the metering chamber.

It is thus the aim of the invention to provide a dosing system for an inhalation device which overcomes any of the limitations of the prior art; e.g. by allowing for a higher dosing flexibility, reducing dosing deviations by minor handling errors and/or considerably decrease the risk of unintentional re-dosing. Another object is to provide a dosing system which is easy for the user to assemble and/or use and which has limited (losable) components. A further object is to provide a dosing system with high dosing accuracy even for small volumes.

SUMMARY OF THE INVENTION

The invention provides dosing systems, an inhalation device with said dosing systems and a method of dosing, meeting one or more of the objectives. Advantageous embodiments are provided in the dependent claims.

In particular, the invention provides a dosing system for an inhalation device, comprising (a) a filling chamber for receiving a liquid to be aerosolized, the filling chamber having a lateral wall, an inlet opening and an outlet opening with a closing means for closing the outlet opening;

(b) an overflow chamber surrounding the inlet opening of the filling chamber; and (c) a plunger which is at least partially insertable into the filling chamber, and which sealingly contacts the lateral wall while being at least partially inserted into the filling chamber such as to push, after the filling chamber has received at least a predefined fill volume of the liquid, a metered volume of the liquid out from the filling chamber through the outlet opening, wherein the metered volume is smaller than the fill volume. The inhalation device may be, or comprise, a nebulizer selected from a vibrating mesh nebulizer, a jet nebulizer, an ultrasonic nebulizer or a Rayleigh spray nebulizer, preferably a vibrating mesh nebulizer. In another embodiment, the nebulizer is selected from a jet nebulizer, an ultrasonic nebulizer and a vibrating mesh nbebulizer. In this case, the mesh of the vibrating mesh nebulizer may be positioned below the outlet opening, and it may have a horizontal orientation while the inhalation device is held in the operating orientation.

In the operating orientation, the inlet opening may be located at the upper end of the filling chamber. The outlet opening may be located at the lower end of the filling chamber, and may be closable by means of a capillary tube, a liquid flow resistor, a nozzle, a valve, a one-way valve, a duckbill valve, a slit valve or a ball valve.

The filling chamber, or the portion of the filling chamber into which the plunger or the insertable portion of the plunger (4) is inserted; and/or the plunger, or the portion of the plunger which is inserted into the filling chamber, may be substantially cylindrical and/or may be of a flexible material.

The filling chamber may be closable prior to and during operation of the inhalation device. For this purpose, the plunger, which may be connectable to, or an integral part, of a lid, may be sized and shaped such as to be capable of closing the filling chamber. The lid may be a flip-top lid. Optionally, the plunger may be connectable to, or be an integral part of, a lid wherein said lid is capable of closing the filling chamber.

The plunger may be at least partially inserted into the filling chamber when closing the lid, thereby pushing a metered volume of liquid—which is smaller than the fill volume—out from the filling chamber through the outlet opening and into the nebulizer and/or onto the nebulizing means. During this at least partial insertion into the filling chamber, the plunger may seal the filling chamber towards the inlet opening such that no liquid leaves the filling chamber through the inlet opening.

The outlet opening of the dosing system may further be surrounded by a residual pocket which is positioned below the outlet opening and into which the plunger cannot be inserted.

Besides the lateral wall of the filling chamber, the dosing system further comprises an outer wall of the overflow chamber, both walls having a respective upper end. A bulge may be formed at the upper end of the lateral wall and/or at the upper end the outer wall of the overflow chamber. Further, the lateral wall has an outer side and the outer wall has an inner side, both facing the overflow chamber. The outer side and/or the inner side may be concavely curved or leaning towards the overflow chamber (5).

The invention further comprises a dosing system for an inhalation device, comprising (a) a nebulizer chamber (7);

(b) an aerosol head component (14);

(c) a filling chamber for receiving a liquid to be aerosolized, formed by the nebulizer chamber (7) and the aerosol head component (14), the filling chamber having a lateral wall, an inlet opening and an outlet opening and a mesh (8) affixed to the outlet opening (3); and (d) a plunger which is at least partially insertable into the filling chamber, and which sealingly contacts the lateral wall of the filling chamber upon being at least partially inserted into the filling chamber after the filling chamber has received at least a predefined fill volume of the liquid such as to isolate a metered volume of the liquid; wherein the metered volume is smaller than the fill volume.

The invention further provides an inhalation device with the dosing system described above.

The invention further provides a method for dosing a liquid to be aerosolized comprising the steps of:

(1) providing a filling chamber for receiving a liquid to be aerosolized, the filling chamber having (a) a lateral wall, (b) an inlet opening and (c) an outlet opening with a closing means for closing the outlet opening;

(2) providing an overflow chamber surrounding the inlet opening of the filling chamber; and (3) providing a plunger which is at least partially insertable into the filling chamber, and which sealingly contacts the lateral wall while being at least partially inserted into the filling chamber such as to push, after the filling chamber has received at least a predefined fill volume of the liquid, a metered volume of the liquid out from the filling chamber through the outlet opening; and

(44) filling the filling chamber with at least a predefined fill volume of the liquid; and (5) at least partially inserting the plunger such as to push a metered volume of the liquid out from the filling chamber through the outlet opening, wherein the metered volume is smaller than the fill volume.

Further advantageous embodiments, optional features, beneficial effects and uses of the device are described below in more detail.

Definitions

The terms "comprise" or "comprising" with reference to any feature means that the respective feature must be present, but without excluding the presence of other features.

"A" or an does not exclude a plurality.

"Essentially", "about", "approximately" and the like in connection with an attribute or value include the exact attribute or the precise value, as well as any attribute or value typically considered to fall within a normal range or variability accepted in the technical field concerned.

"Upper" and "lower", such as in "upper end" and "lower end", as well as all similar terms designating a position, orientation or direction, such as left, right, front, back, top, bottom, up, down, superior, inferior and the like, should be understood with reference to the orientation of the inhalation device or its components under normal operational conditions, and typically from the perspective of the user. This orientation is also referred to as the operating orientation and describes how the user is supposed to hold the device during operation, with minor deviations being allowed.

As used herein, the "predefined fill volume" is the minimum volume which must be filled into the filling chamber in order to achieve reproducible dosing. Depending on the configuration of the dosing system, the volume of liquid actually filled into the filling chamber may be slightly or even substantially larger than the predefined fill volume, or minimum fill volume.

The liquid can be provided, for instance, in pre-filled single-use containers, such as vials, or ampoules, as commonly available for many commercialized inhalative medications. The fill volume may vary between containers, and the volume withdrawn from a container may also depend on the user. The invention provides a means for delivering a prescribed dose of inhalation liquid in aerosol form in spite of these variations.

The "metered volume", as used herein, is the predefined volume of liquid which the dosing system feeds to the aerosol generator, and which is converted into an aerosol delivered to the user. The metered volume is a part of the fill volume.

An "aerosol generator" is a device or device component capable of generating an aerosol.

A "nebulizing means" is an aerosol generator which generates an aerosol from a liquid. The aerosol comprises a liquid phase consisting of small, typically inhalable droplets dispersed in a gas phase such as air.

The term "overflow chamber" as used herein refers to a chamber associated with the dosing system or parts thereof, which takes up a fraction of any volume in excess to the metered volume, irrespective of whether this fraction is spontaneously (over)flowing due to gravity or whether it is actively transferred during operation of the dosing system; e.g. by displacement.

As also in the current technical literature, a "nebulizer" may refer to a nebulizing means to an inhalation device comprising a nebulization means, depending on the context.

Any reference signs in the claims should not be construed as a limitation to the embodiments represented in any of the drawings.

A single unit may fulfill the functions of several features recited in the claims.

BRIEF DESCRIPTION OF THE DRAWINGS

FIGS. 10A-B show a dosing system according to an embodiment of the invention in open state (A) and in closed state (B); dashed lines represent exemplary liquid levels

Figure 1:
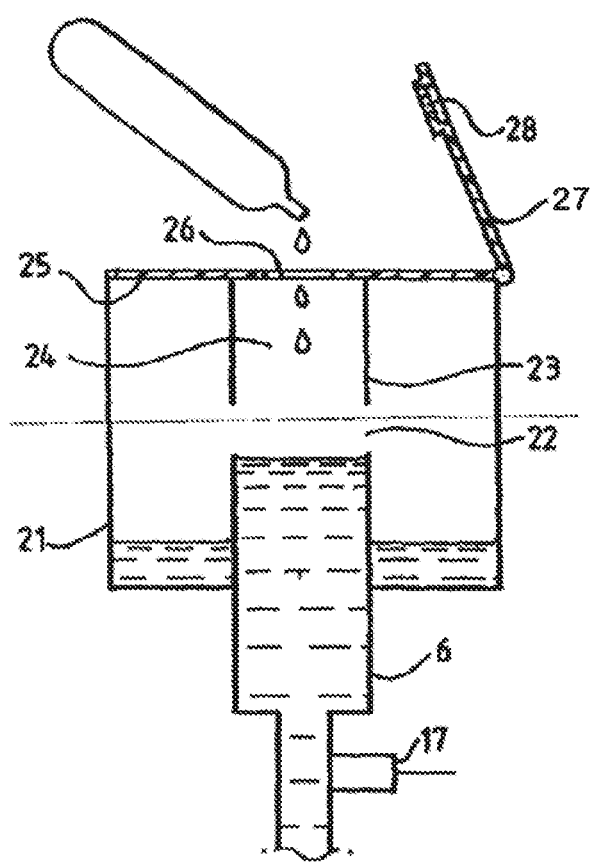
FIG. 1 shows a prior art dosing system for a nebulizer as disclosed in EP 1 465 692 B1

With regard to all figures it is to be understood that they merely represent construction principles and are not necessarily up to scale.

LIST OF NUMERICAL REFERENCES USED IN THE FIGURES

| | |
|---|---|
| 1, 1a | Filling chamber |
| 2 | Inlet opening |
| 3 | Outlet opening |
| 4 | Plunger |
| 5, 5a | Overflow chamber |
| 6 | Nebulizing means |
| 7 | Nebulizer chamber |
| 8 | Mesh |
| 9 | Lid |
| 10 | Hinge |
| 11 | Duckbill valve |
| 12 | Residual pocket |
| 13 | Snap fit lock |
| 14 | Aerosol head component |
| 15 | Housing (of filling chamber) |
| 16 | Fixture |
| 17 | Annular groove |
| 18 | Central opening |
| 19 | Low resistance one-way valve |
| 20 | Dosing funnel |

-continued

| | |
|---|---|
| 21 | Overflow slits |
| 22 | Slit valve |
| 23 | Release pin |
| 24 | Down pipe |
| 25 | Sealing edge |
| 26 | Safety plunger |
| 27 | Vial |
| 28 | Separation chamber |
| 29 | Upper section of filling chamber |
| 30 | Funnel ribs |
| 31 | Sealing lip |
| 32 | Cartridge port |
| 33 | Puncture pin |
| 34 | Central cylinder of lid |
| 35 | Central cylinder of aerosol head |
| 36 | Gasket component |
| 37 | Gasket |
| 38 | One-way-valve |
| 39 | Channel (in plunger) |
| 40 | Central stopper |
| 41 | Central gasket opening |
| 42 | Lateral wall |
| 43 | Funnel wall |
| 44 | Bulge (overhang) |
| 45 | Outer wall |
| 46 | Outer side of lateral wall |
| 47 | Inner side of outer wall |

DETAILED DESCRIPTION OF THE INVENTION

The invention provides a dosing system for an inhalation device, comprising
(a) a filling chamber for receiving a liquid to be aerosolized, the filling chamber having a lateral wall, an inlet opening and an outlet opening with a closing means for closing the outlet opening;
(b) an overflow chamber surrounding the inlet opening of the filling chamber; and
(c) a plunger which is at least partially insertable into the filling chamber, and which sealingly contacts the lateral wall while being at least partially inserted into the filling chamber such as to push, after the filling chamber has received at least a predefined fill volume of the liquid, a metered volume of the liquid out from the filling chamber through the outlet opening, wherein the metered volume is smaller than the fill volume.

In other words, the volume which is displaceable by the plunger, or the volume of the plunger which is insertable into the filling chamber, is smaller than the predefined fill volume.

An exemplary inhalation device is described for example in WO2013098334A1 or co-pending EP application no. 12 190139.1.

In one embodiment, the inhalation device is, or comprises, a nebulizer selected from ultrasonic nebulizers, jet nebulizers or vibrating mesh nebulizers. In a more specific embodiment the nebulizer is a vibrating mesh nebulizer.

The dosing system has an operating orientation, and the filling chamber of the dosing system has an upper end and a lower end. In one embodiment, when in operating orientation, the inlet opening is located at the upper end of the filling chamber and the outlet opening is located at its lower end. The liquid to be aerosolized may flow from the inlet opening towards the outlet opening when the filling chamber is filled.

In one embodiment, the outlet opening of the dosing system is closable by means of a capillary tube, a liquid flow resistor, a nozzle, a valve, a one-way valve, a duckbill valve, a slit valve or a ball valve.

In one embodiment, the outlet opening of the dosing system is in fluid connection with an aerosol generator; i.e. the outlet opening is not closed by a closing means but instead is located at a higher level than the inlet opening when in operating orientation.

In the embodiment using a vibrating mesh nebulizer, the mesh of the vibrating mesh nebulizer may be positioned below the outlet opening and may have a horizontal orientation when in operating orientation.

The filling chamber has a portion into which the plunger or an insertable portion of the plunger (4) is inserted. Vice versa, the plunger is inserted, or has a portion which is inserted, into the filling chamber. In one embodiment, the filling chamber, or the portion of the filling chamber into which the plunger or the insertable portion of the plunger is inserted, and/or the plunger, or the portion of the plunger that is inserted into the filling chamber, may be somewhat cylindrical in overall shape, or even substantially cylindrical. In this case, the cylindrical filling chamber may have a vertical, or approximately vertical orientation under operating conditions. Optionally, the filling chamber, or the portion of the filling chamber into which the plunger or the insertable portion of the plunger is inserted; and/or the plunger, or the insertable portion of the plunger, may also have quite different shapes; e.g. polygonal or "doughnut-shaped" with the plunger being the convex part and the filling chamber being the concave counterpart. In any case, the volume displaceable by the plunger, or the volume of the plunger insertable into the filling chamber, is always smaller than the predefined fill volume.

In one embodiment, the filling chamber, or the portion of the filling chamber into which the plunger or the insertable portion of the plunger is inserted; and/or the plunger, or the insertable portion of the plunger, may be made of a flexible material. In particular, a flexible plunger may be combined with a rigid filling chamber, or a rigid plunger may be combined with a flexible filling chamber.

In one embodiment, the filling chamber is closable prior to and during the operation of the inhalation device; i.e. before and during the onset of nebulization.

In one embodiment, the dosing system comprises a lid and the plunger is connectable to, or an integral part, of the lid, and may be sized and shaped such as to be capable of closing the filling chamber such as to be capable of closing the filling chamber. Alternatively, the plunger is connectable to, or an integral part of, the lid and the lid is capable of closing the filling chamber. In a more specific embodiment, the plunger is at least partially inserted into the filling chamber when the lid is closed. In a more specific embodiment, the lid is a flip-top lid; preferably a lid attached with an off-centered hinge.

In one embodiment, the plunger seals the filling chamber towards the inlet opening during its at least partial insertion into the filling chamber, such that no liquid leaves the filling chamber through the inlet opening.

In one embodiment, the outlet opening is surrounded by a residual pocket which is positioned at a lower level than the outlet opening and into which the plunger cannot be inserted. Optionally, such residual pocket is divided into a plurality of compartments.

Besides the lateral wall of the filling chamber, the dosing system further comprises an outer wall of the overflow chamber; each having a respective upper end. In one embodiment, a bulge (or rim) is formed at the upper end of the lateral wall of the filling chamber and/or at the upper end of the outer wall of the dosing system.

Alternatively, or in addition to the bulge, the lateral wall of the filling chamber has an outer side facing the overflow chamber and the outer wall of the overflow chamber has an inner side facing the overflow chamber. One or both sides may be concavely curved or leaning towards the overflow chamber. These features, i.e. the bulge and/or the curvature or angle, help to prevent unintentional or accidental re-dosing even when the dosing system is tilted from the operating orientation. They prevent, or partially prevent, liquid from flowing from the overflow chamber to the filling chamber when the device is tilted.

The invention further comprises a dosing system for an inhalation device, comprising
 (a) a nebulizer chamber (7);
 (b) an aerosol head component (14);
 (c) a filling chamber for receiving a liquid to be aerosolized, formed by the nebulizer chamber (7) and the aerosol head component (14), the filling chamber having a lateral wall, an inlet opening, an outlet opening and a mesh affixed to the outlet opening; and (d) a plunger which is at least partially insertable into the filling chamber, and which sealingly contacts the lateral wall of the filling chamber upon being at least partially inserted into the filling chamber after the filling chamber has received at least a predefined fill volume of the liquid such as to isolate a metered volume of the liquid; wherein the metered volume is smaller than the fill volume.

The inventors have found that, in comparison to the currently known dosing systems, the dosing system of the invention is more precise, accurate and reproducible in regards to the dosed volume, in particular for small doses such as below 0.3 mL. Some prior art relies on an overflow principle, and the liquid flow could directly influence the dosing system, which makes the prior art system more liable to being impacted by e.g. surface tension and viscosity of the filled inhalation solution. The here invented device reduces the influence of liquid properties to a minimum. The actually metered volume is controlled by the well-defined displacement, or pumping effect, of the plunger, in combination with the well-defined opening pressures of the valve(s). At the same time, any excess volumes of liquid which are not supposed to be administered to the user are isolated in a separate overflow chamber and cannot be re-dosed accidentally, which increases the operational safety of the dosing device.

The invention further provides an inhalation device with the dosing system according to the invention.

The invention further provides a method for dosing a liquid to be aerosolized comprising the steps of:

(1) providing a filling chamber (1) for receiving a liquid to be aerosolized, the filling chamber having (a) a lateral wall, (b) an inlet opening and (c) an outlet opening with a closing means for closing the outlet opening (2) providing an overflow chamber surrounding the inlet opening of the filling chamber; and (3) providing a plunger which is at least partially insertable into the filling chamber, and which sealingly contacts the lateral wall while being at least partially inserted into the filling chamber such as to push, after the filling chamber has received at least a predefined fill volume of the liquid, a metered volume of the liquid out from the filling chamber through the outlet opening; and (4) filling the filling chamber with at least a predefined fill volume of the liquid; and (5) at least partially inserting the plunger such as to push a metered volume of the liquid out from the filling chamber through the outlet opening, wherein the metered volume is smaller than the fill volume.

Preferred embodiments of the invention will now be described in further detail and with regard to FIGS. 2-14.

FIGS. 2A-C show a dosing system according to a specific embodiment of the invention, comprising (a) a substantially cylindrical filling chamber (1) for receiving a liquid to be aerosolized, the filling chamber having a substantially circular inlet opening (2) and a substantially circular outlet opening (3) which is closed by a duckbill valve (11) such as to prevent the liquid received by the filling chamber (1) from flowing through the outlet opening (3) by gravity;

(b) an overflow chamber (5) surrounding the inlet opening (2) of the filling chamber (1); and (c) a substantially cylindrical plunger (4) which is at least partially insertable into the filling chamber (1), and which sealingly contacts the lateral wall (42) while being at least partially inserted into the filling chamber (1) such as to push, after the filling chamber (1) has received at least a predefined fill volume of the liquid, a metered volume of the liquid out from the filling chamber (1) through the outlet opening's duckbill valve (11), wherein the metered volume is smaller than the fill volume.

While other shapes of the filling chamber may be feasible, too, the cylindrical shape chosen in this particular embodiment allows for an easier insertion of the plunger (4), especially since in this embodiment the plunger (4) is initially inserted into the filling chamber (1) at a slight angle to the filling chamber's longitudinal axis, as can be seen in FIG. 2B. In this case, the plunger (4) is an integral part of a lid (9) which is fixed with a hinge (10) at an off-centered position. The filling chamber (1) is accommodated within a housing (15) affixed to the same hinge (10). An exploded view of a lid assembly with a hinge is depicted in FIG. 5. Such flip-top lid assemblies are preferred for the present invention from a user's perspective, since they reduce the number of components which may be lost and/or assembled incorrectly.

In the embodiment shown in FIGS. 2A-C, the filling chamber (1) is closable prior to and during operation of the inhalation device. More specifically, the plunger (4) is at least partially inserted into the filling chamber (1) when closing the lid. During its insertion, the plunger (4) seals the filling chamber (1) towards the inlet opening (2) such that no liquid leaves the filling chamber (1) through the inlet opening (2). This is achieved by the plunger (4) being sized and shaped such as to be capable of closing the filling chamber. Since the size and shape of the plunger (4) in this specific embodiment matches the size and shape of the inlet opening (2) of the filling chamber (1) (both being cylindrical, the outer diameter of the plunger (4) corresponding to the inner diameter of the filling chamber (1) and the length of the plunger (4) being similar to, or slightly shorter than, the height of the filling chamber (1)), the plunger (4) itself closes and seals the inlet opening (2) during its insertion into the filling chamber (1). The contact between the plunger (4) and the filling chamber's lateral wall (42) at the inlet opening (2) is further enhanced by the fact that the filling chamber's lateral wall (42) is made of a flexible material and tilts slightly towards the plunger (4), as also shown in the enlarged views in FIGS. 3A and B. This is advantageous because no further sealing means are required; such as the additional O-ring seals around the plunger (4) used in some of the prior art. In addition, this allows the plunger (4) to slide smoothly into the filling chamber (1) and avoids undesirable friction below the inlet opening (2).

It should be noted, though, that in other embodiments which provide for a different closing and/or sealing mechanism of the filling chamber (1) at the inlet opening (2), it may not always be necessary that the plunger (4) is sized and shaped such as to match the size and shape of the inlet opening (2) in order to allow the plunger (4) to reproducibly displace liquid and push it through the outlet opening (3). For instance, the plunger (4) could have the same shape and a precisely fitting diameter, but may have a length shorter than that of the filling chamber; or the plunger may have the same shape and a precisely fitting diameter only at the plunger's tip (the plunger part which is inserted into the filling chamber first) while the rest of the plunger may have a different shape and diameter.

In other embodiments, as will be shown in FIGS. 8A and B below, the plunger may not even have to close and seal the complete inlet opening (2) in order to displace the metered volume from the filling chamber (1).

Figure 2A:
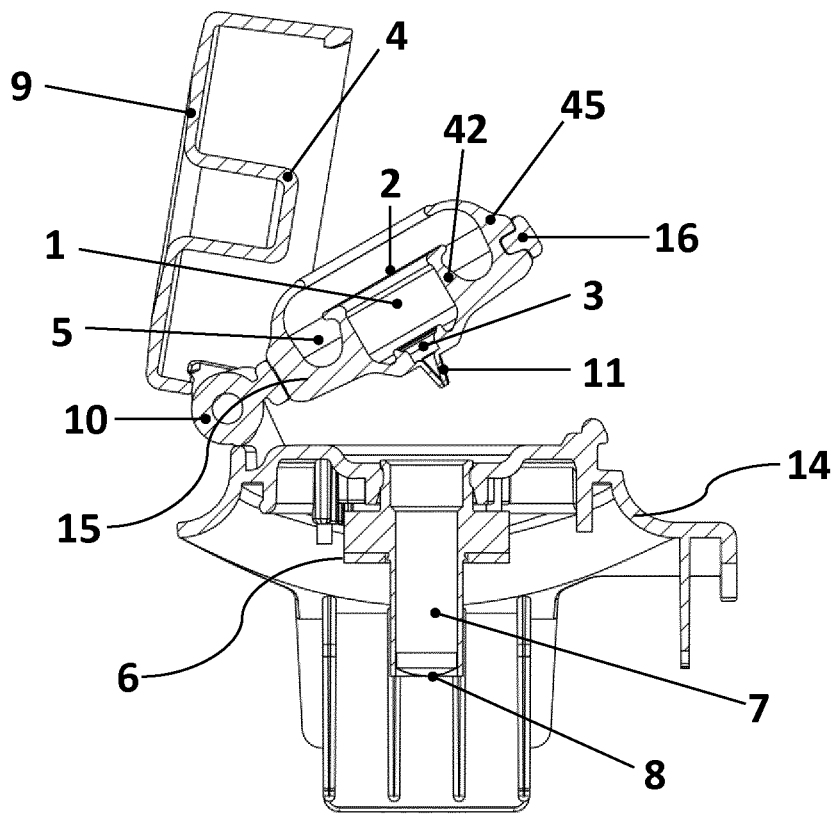
FIGS. 2A-C show a dosing system according to an embodiment of the invention
Figure 2B:
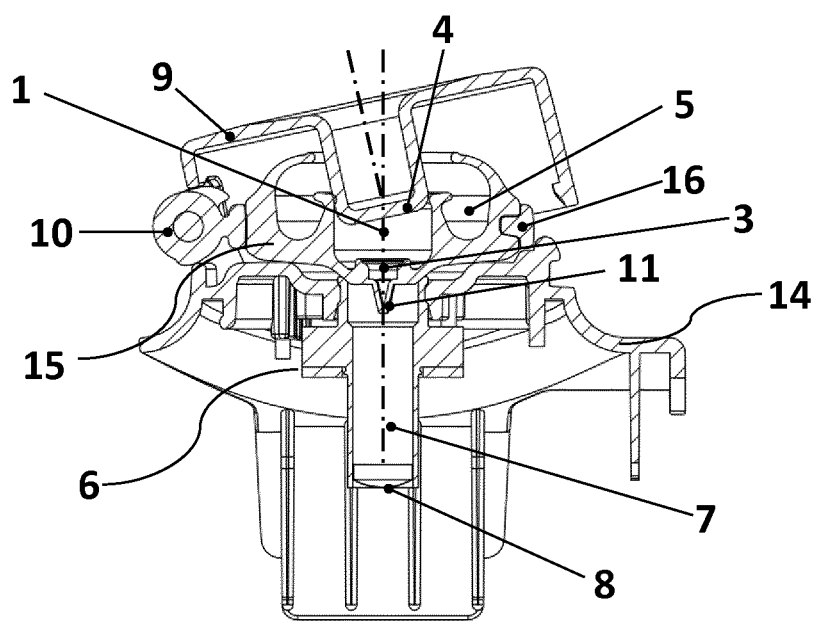

The insertion of the plunger (4) at a slight angle depicted in FIG. 2B—as it will occur with the hinged-lid-plunger-assembly (10, 9, 4)—typically requires a certain degree of flexibility in the materials of the filling chamber (1) and/or the plunger (4). Examples of such flexible materials are silicone and thermoplastic elastomers (TPE). Optionally, only one part is made of a flexible material such as silicone or thermoplastic elastomers, while the respective counterpart is prepared from a hard and/or inflexible material. Examples of such hard and/or inflexible materials are polyoxymethylene (POM; also known as acetal, polyacetal or polyformaldehyde) or polypropylene (PP), polyether-etherketone (PEEK) and polyamide (PA).

With regard to all materials used in a dosing system according to the present invention, it should be understood that the use of biocompatible plastics and elastomers (see ISO 10993) is preferred wherever feasible. It is to be understood, that the above mentioned materials are not limited to the embodiment shown in FIGS. 2A-C but are equally applicable to other embodiments of the present invention.

An overflow chamber (5) surrounds the inlet opening (2) of the filling chamber (1), e.g. circumferentially, in order to receive any excess volume of liquid which cannot be contained within the filling chamber (1). This offers the important advantage that the excess volume in the overflow chamber (5) is prevented from unintentionally flowing back into the filling chamber (1) upon withdrawal of the plunger (4) from the filling chamber (1) after the dosing step; i.e. after the step of closing the lid (9) and thereby moving the plunger (4) to its final position within the filling chamber (1). This reduces the risk of unintentional or accidental re-dosing or even overdosing.

A bulge (44), such as a rim, may be formed at the upper end of the lateral wall (42) and/or at the upper end of the outer wall (45) of the overflow chamber. Optionally, the bulge (44) may be leaning towards the overflow chamber (5) and away from the filling chamber (1). Such a bulge (44) at the upper end of the lateral wall (42) can be seen exemplarily in FIGS. 2A to 4, in particular in the enlarged views of FIGS. 3A and B.

Alternatively to the bulge (44), or in addition to it, the outer side (46) of the lateral wall (42) facing the overflow chamber (5) and/or the inner side (47) of the outer wall (45) facing the overflow chamber (5) may be concavely curved or leaning towards the overflow chamber (5). Both, the bulge (44) and/or the orientation and shape of the outer and inner sides (46 and 47) facing the overflow chamber (5), reduce the risk of unintended re-dosing even further, because even if the device is tilted a bit by the user, or moderately moved out of the operating orientation, the excess volume of liquid contained in the overflow chamber (5) is prevented from flowing back into the filling chamber (1) upon withdrawing the plunger (4) from the filling chamber (1).

Prior to the use of the inhalation device, a volume of liquid to be nebulized is filled into the filling chamber (1). The actual fill volume matches or exceeds the minimal fill volume, also referred to as pre-defined fill volume. The liquid may be withdrawn from single-use container as available for many commercialized inhalative medications. For this purpose, the inhalation device is best placed on an even surface, the lid (9) opened wide with the housing (15) resting on the aerosol head component (14). Then the pre-filled fill volume can be poured easily through the wide top opening of the housing (15) and through the inlet opening (2) into the filling chamber (1). If more liquid is filled into the device than can be held by the filling chamber (1), some of the liquid may flow into an overflow chamber (5).

Figure 2C:
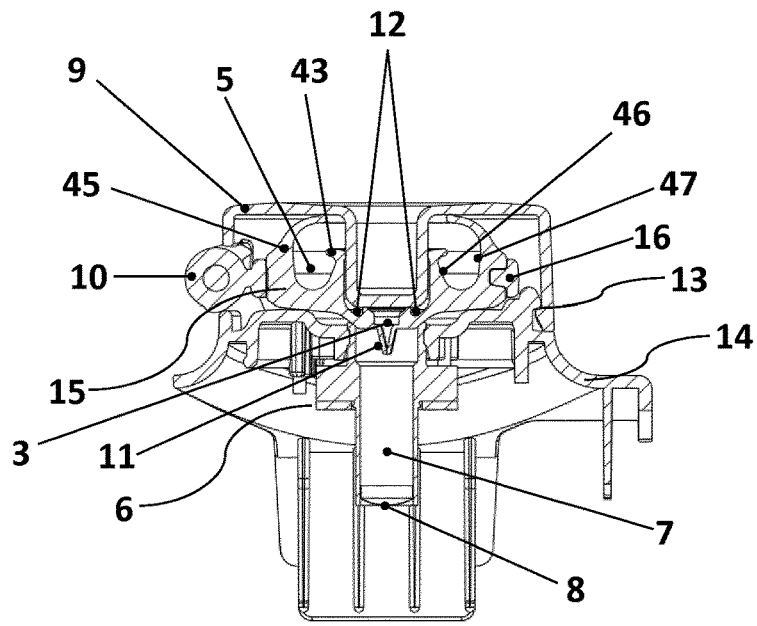
Figure 3A:
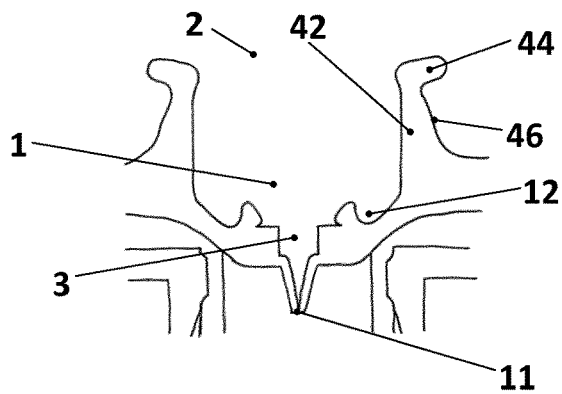
FIGS. 3A-B show a duckbill valve for a dosing system according to an embodiment of the invention, provided as a separate part (B) or as an integral part (A) of the filling chamber's outlet opening (3)
Figure 3B:
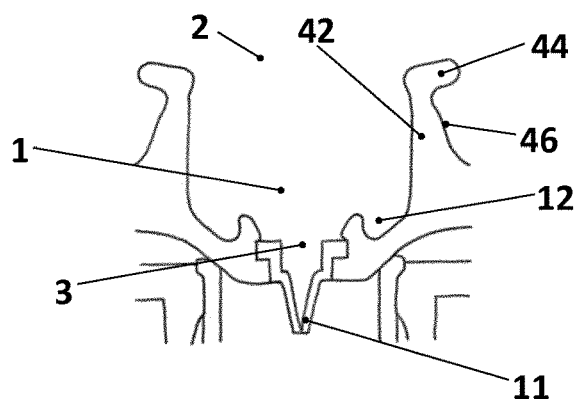
Figure 4:
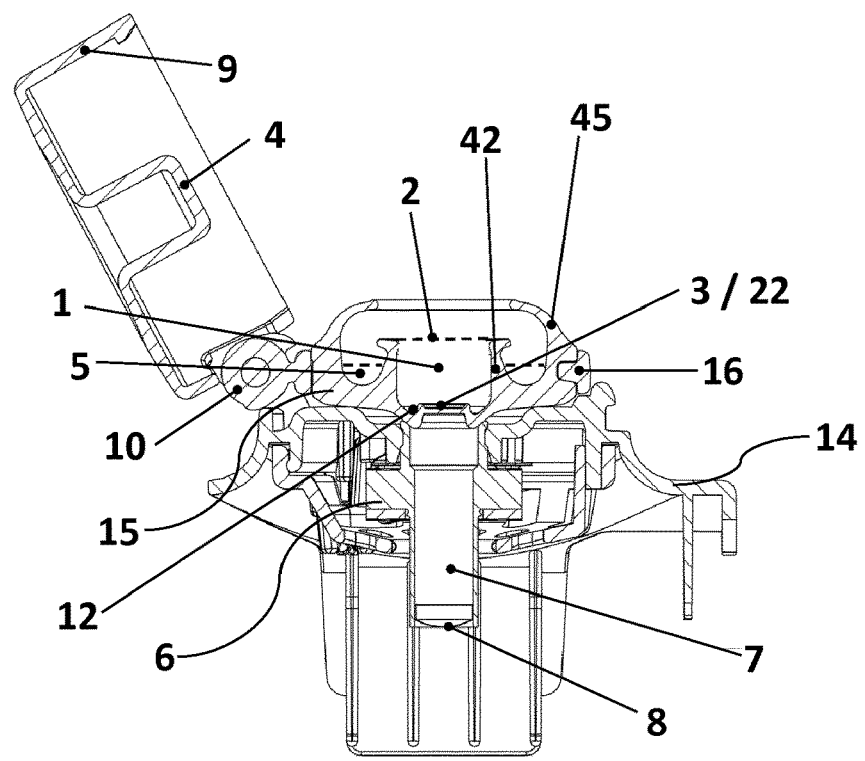
FIG. 4 shows a dosing system according to an embodiment of the invention in open state with the fill component folded down
Figure 5:
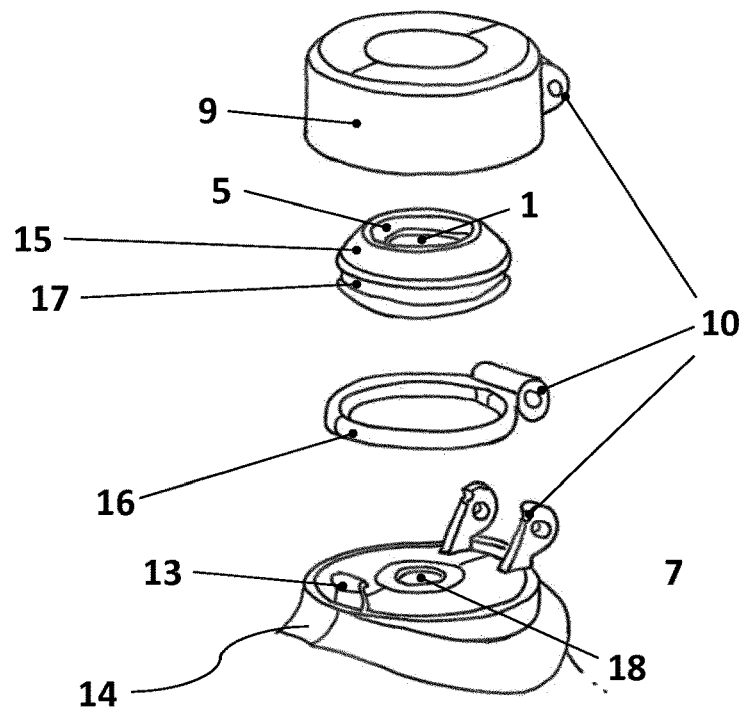
FIG. 5 shows an exploded view of the hinged components of a dosing system according to an embodiment of the invention

The pre-defined (or minimum) fill volume is at least slightly larger than the metered volume. In the embodiment of FIGS. 2A-C, the overflow chamber (5) surrounds the inlet opening (2) of the filling chamber (1) and/or the filling chamber (1) circumferentially.

In this embodiment, the plunger (4) is inserted into the filling chamber (1) by closing the filling chamber (1) with the hinged lid (9), thereby displacing a part of the liquid in the filling chamber (1), which is pushed out through the duckbill-valve (11) of the outlet opening (3). However, the plunger (4) is not inserted, or insertable, into the overflow chamber (5).

In principle, the plunger (4) may be directly immersed into the liquid filled into the filling chamber (1). Alternatively, the dosing system may also be configured such that plunger (4) is not immersed into the liquid upon its insertion into the filling chamber (1). In this case, the metered volume of liquid is indirectly displaced by the plunger (4) via entrapped air.

The outlet opening (3) is in fluid connection with the nebulizing means (6), or aerosol generator. Here, the metered volume of liquid which is pushed through the outlet opening (3) will flow freely into the nebulizing means (6); more specifically into the nebulizing means' (6) internal cavity, herein also called the nebulizer chamber (7). In order to avoid premature, non-metered flow of liquid through the outlet opening (3) upon filling, the outlet opening is closable by means of a capillary tube, a liquid flow resistor, a nozzle, a valve, a one-way valve, a slit valve, a ball valve, or a duckbill valve (11) as shown in FIGS. 2A-C, at least to the extent as to prevent the liquid received by the filling chamber from flowing through the outlet opening by gravity.

Figure 6A:
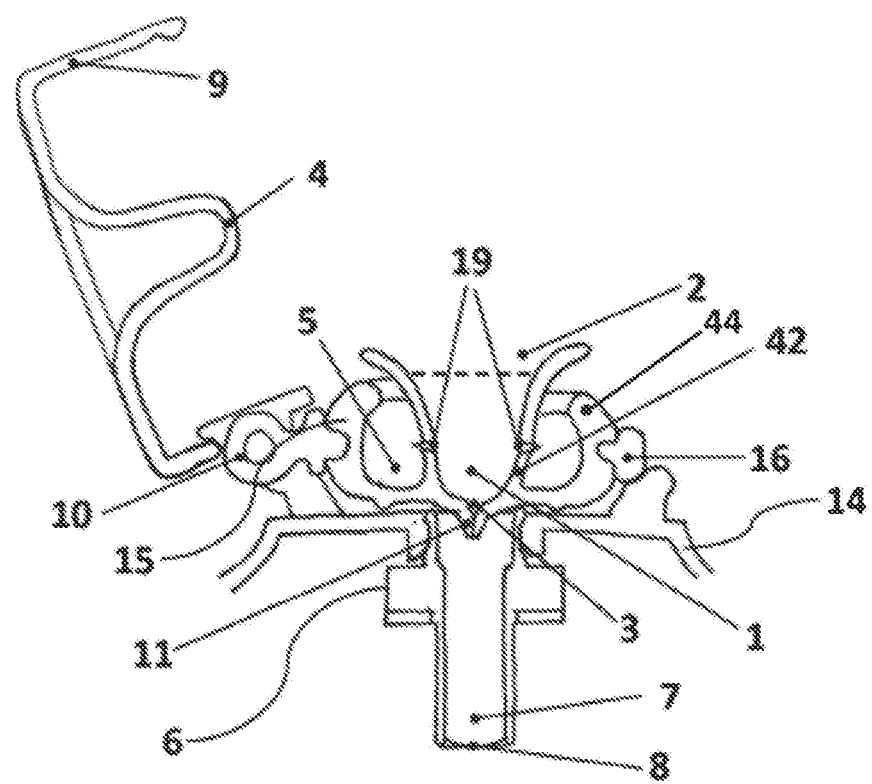
FIGS. 6A-B show a dosing system according to an embodiment of the invention in open state (A) and in closed state (B); dashed lines represent exemplary liquid levels
Figure 6B:
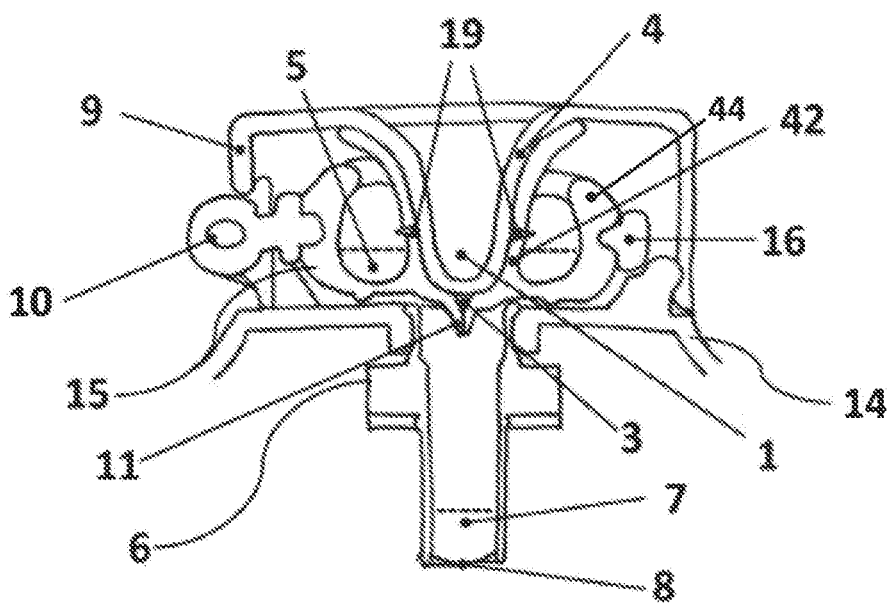

The embodiment in FIGS. 2A-C shows a vibrating mesh nebulizer as the nebulizing means (6). An exemplary nebulizing means according to this invention is described e.g. in EP 2 091 663 B1. The mesh (8) of the vibrating mesh nebulizer is positioned below the outlet opening (3) and has a horizontal orientation while the inhalation device is held in the operating orientation. The nebulizing means (6) comprises an internal cavity for containing the liquid to be aerosolized, the nebulizer chamber (7). The volume of the nebulizer chamber (7) is larger than the target volume to be metered so that the metered volume can be accommodated completely within the nebulizer chamber (7). The liquid is held in the nebulizer chamber (7) by the horizontally arranged mesh (8) until the onset of operation of the vibrating mesh nebulizer. Then the mesh (8) will be vibrated, e.g. by a piezo-electric ceramic element, and the liquid will gradually be passed through the mesh (8) in the form of minute droplets.

Optionally, there may be provided a small opening for venting (not shown in FIGS. 2 A-C) in the lateral wall of the nebulizing means (6) to avoid the build-up of any underpressure when the liquid in the nebulizer chamber (7) is gradually removed by nebulization through the mesh (8). Preferably, such an opening should be positioned slightly below the outlet opening (3), but above the uppermost level of the liquid column resting in the nebulizer chamber (7), such that none of the metered volume is lost through said venting opening. Optionally, this opening may also be provided with a one-way valve to prevent any loss of the metered volume of liquid even if the user tilts the inhalation device.

The volume of liquid pushed through the outlet opening (3) is metered by displacement, i.e. by the volume of the plunger (4), or the respective portion of the plunger (4), which is inserted into the filling chamber (1). Therefore, only small changes in the geometry of the plunger, such as the length of the plunger, are required to adjust the metered volume to a different target volume, thus providing a major advantage over prior art systems. For instance, different plungers could be provided for the different doses required for adults, kids and infants or to account for dose adaptations that can become necessary when the condition of a patient changes. Moreover, a plunger with a variable insertion depth may be used, and the insertion depth may be adjusted e.g. by a wheel. This greatly improves the flexibility of dosing because only a small, inexpensive, exchangeable and easy-to-manufacture part has to be exchanged. A color-coding system and/or an embossed letter at the top of the plunger, for instance, may optionally be used to allow for a clear and easy distinction between different plungers.

In some cases, a plunger (4) which is connectable to the lid (9) (rather than being an integral part of it as shown in FIGS. 2A to C) may be more advantageous, because it could be exchanged more easily and/or with less material consumption than exchanging the whole lid (9). On the other hand, small exchangeable components such as the plunger (4) may easily get lost when not connected to the lid; e.g. the may fall into the sink during the cleaning of the dosing system. They may also be harder to handle for elderly and kids. Thus, both options should be considered with care and with regard to the potential user.

FIG. 2C shows the plunger (4) after its complete insertion, i.e. when the lid (9) is fully closed and shut by a snap-fit-lock (13). At the bottom of the filling chamber (1), a residual pocket (12) surrounds the outlet opening (3), from which liquid cannot be pushed out while the plunger (4) is at least partially inserted into the filling chamber (1). This is because the residual pocket is positioned at a lower level than the outlet opening (3) and further because the plunger cannot be inserted into the residual pocket even when the plunger reaches its final position in the filling chamber. Such a residual pocket (12) can be used to increase the tolerance of the dosing system to variable fill volumes of liquid filled into the filling chamber (1), in particular for small metered volumes, and may reduce the need for large overflow chambers (5). An enlarged view of the outlet opening (3), duckbill valve (11) and the residual pocket (12) can also be seen in FIGS. 3A and B.

Depending on the design of the outlet opening (3) and its closing mechanism, a small residual volume may be difficult to avoid even if a distinct residual pocket (12) were not present.

The residual pocket (12) should preferably be positioned and shaped such as to minimize the risk of accidental re-dosing, e.g. by opening and closing the lid (9) after nebulization without first emptying and cleaning the device. Unintended opening and closing of the lid (9) after the dosing step is also impeded by the snap-fit lock (13).

The duckbill valve (11), or any other means for closing the outlet opening (3) at least to the extent as to prevent the liquid received by the filling chamber (1) from flowing through the outlet opening (3) by gravity, such as a capillary tube, liquid flow resistor, nozzle, valve, one-way valve, duckbill valve, slit valve or ball valve, may be formed as an integral part of the filling chamber's outlet opening (3) as shown in FIG. 3A, or alternatively as a separated part which is attached, insertable and/or connectable to the dosing system's filling chamber and/or outlet opening; e.g. by a snap-fit mechanism, as shown in FIG. 3B.

An alternative embodiment of a dosing system provided with a slit valve (22)—instead of a duckbill valve (11)—closing the outlet opening (3) is shown in FIG. 4, with the dashed lines representing the fill level in the filling chamber (1) and an exemplary fill level in the overflow chamber (5). Exemplary slit valves are single slit or cross slit valves.

An exploded view of the hinged components of the dosing systems depicted in FIG. 2A-C or 4 is depicted in FIG. 5. Hinged flip-top lids advantageously allow for simple yet reproducible closing, opening, and cleaning, while at the same time reducing the risks of incorrect assembly and/or loss of any loose parts. The assembly shown in FIG. 5 comprises a lid (9) with the plunger (not shown), a housing (15) for the filling chamber (1), a fixture (16) and an aerosol head component (14). The aerosol head component (14) comprises, or is connected to, the nebulizing means (6) (not shown), a central opening (18) to allow for fluid connection between the dosing system's outlet opening (3) and the nebulizer chamber (7) and one part of the snap-fit lock (13) which secures the lid (9) upon closure. An exemplary aerosol head component (14) with a nebulizing means (6) is described e.g. in EP application no. 12190139.1.

The housing (15) comprises the filling chamber (1) with its inlet- and outlet openings (2, 3) and the overflow chamber (5), and has an annular groove (17) around its circumference. The annular groove (17) allows for the correct and secure placement of the housing (15) in the fixture (16) via a snap-fit. Like the lid (9) and the aerosol head component (14), this fixture (16) comprises a part which upon assembly and connection with a bolt (not shown) forms a sturdy hinge (10). One of the purposes of providing a housing (15) with a separate fixture (16) is to allow an easy exchange of the housing (15) without the need to unhinge all components. The hinge (10) can be configured with different latching positions so as to allow the user to more easily space apart the lid (9), the housing (15) in its fixture (16) and the aerosol head component (14), without the need to hold them apart manually. This is particularly useful e.g. when cleaning the device with water after the inhalation. At the same time, such latching positions can be applied to prevent the housing (15) in its fixture (16) from being flipped off from the aerosol head component (14) at angles of more than e.g. 45-55°. Like this, when the inhalation device is placed on an even surface for filling, the housing (15) "shields" the opening of the nebulizer chamber (7) and thereby guides the user not to fill the nebulizer chamber (7) rather than the housing (15).

The embodiment depicted in FIGS. 6A-B, is particularly suitable for relatively large fill volumes from which only a relatively small portion is metered and fed to the nebulizing means. The dashed line indicates an exemplary liquid level after filling the filling chamber (1). Again, the overflow chamber (5) may optionally surround the inlet opening (2) of the filling chamber (1) and/or the filling chamber (1) itself circumferentially. The lateral wall of the filling chamber (1) widens towards the inlet opening such as to prevent the user from accidentally filling liquid into the overflow chamber (5), which decreases the risk for potential dosing inaccuracies.

One or more outlets, here in the form of low-resistance one-way valves (19), are provided in the lateral wall of the filling chamber (1). Their function is to allow liquid to flow, or be pushed, from the filling chamber (1) into the overflow chamber (5) until a predefined liquid level in the filling chamber (1) is reached. Typically, this pre-defined liquid level is similar to, or the same as, the pre-defined fill volume. Depending on the resistance of the valve(s) (19), the flow of liquid into the overflow chamber (5) requires some pressure, e.g. as exerted during the initial phase of the insertion of the plunger (4) into the filling chamber (1). The one-way valve(s) (19) also prevent(s) liquid from flowing back from the overflow chamber (4) into the filling chamber (1), thus further reducing the risk of dosing inaccuracy. In any case, the resistance of the one-way valves (19) is lower than that of the duck-bill valve (11).

Further inserting the plunger (4), i.e. beyond the level of the lateral one-way valve(s) (19), causes the displacement of the metered volume of liquid which is pushed from the filling chamber (1) through the outlet opening (3) via the duck-bill valve (11).

Optionally, the embodiment of FIGS. 6A-B may also be equipped with a residual pocket (12).

FIG. 6B shows the plunger (4) after its completed insertion, i.e. when the lid (9) is fully closed and shut by the snap-fit lock (13). The length of the plunger (4) is the maximum length in combination with the filling chamber (1) reaching down all the way to the outlet opening (3), so that almost all of the liquid in the filling chamber (1) which was not pushed through the low resistance one-way valve(s) (19) is displaced and pushed out through the duckbill valve (11).

It should be noted, though, that—as with all embodiments described and/or depicted—the plunger (4) can have various lengths, shapes and/or volumes to allow for dosing flexibility. Depending on the size and shape of the plunger (4) relative to that of the filling chamber (1), the metered volume may be a relatively small or a relatively large portion of the fill volume.

Depending on the specific dimensions chosen for the plunger (4), there may be embodiments wherein the lid (9) is capable of closing the filling chamber (1), not the plunger (4) itself; e.g. if a cylindrical plunger has a smaller diameter than the respective cylindrical filling chamber so that no seal would be formed between plunger and the filling chamber walls.

The plunger (4) may be either an integral part of the lid (9) or it may be connectable to it. If the plunger (4) is connectable to the lid (9), the connection between lid (9) and plunger (4) may be designed to allow an easy exchange of the plunger (4) (e.g. when the dose required by the patient changes), while at the same time being sturdy enough to prevent unintentional loss of the plunger, e.g. during the cleaning routine. In analogy, if the plunger is an integral part of the lid, the connection between lid (9) and hinge (10) may be designed to allow an easy exchange of the lid, while at the same time being sturdy enough to prevent unintentional loss of the lid.

Figure 7A:
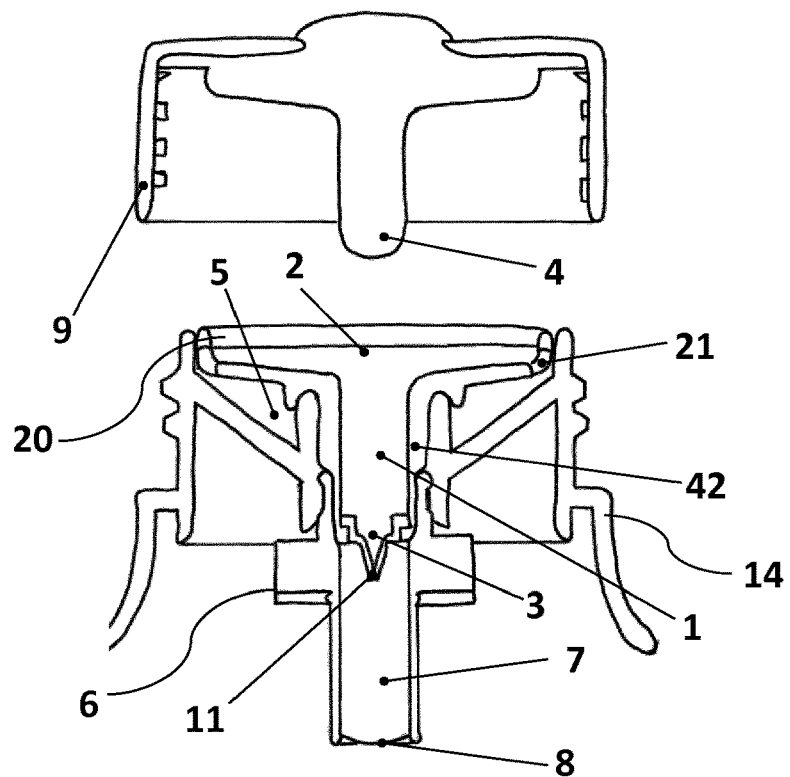
FIGS. 7A-C show a dosing system according to an embodiment of the invention in open state (A), upon insertion of the plunger (B) and in closed state (C)
Figure 7B:
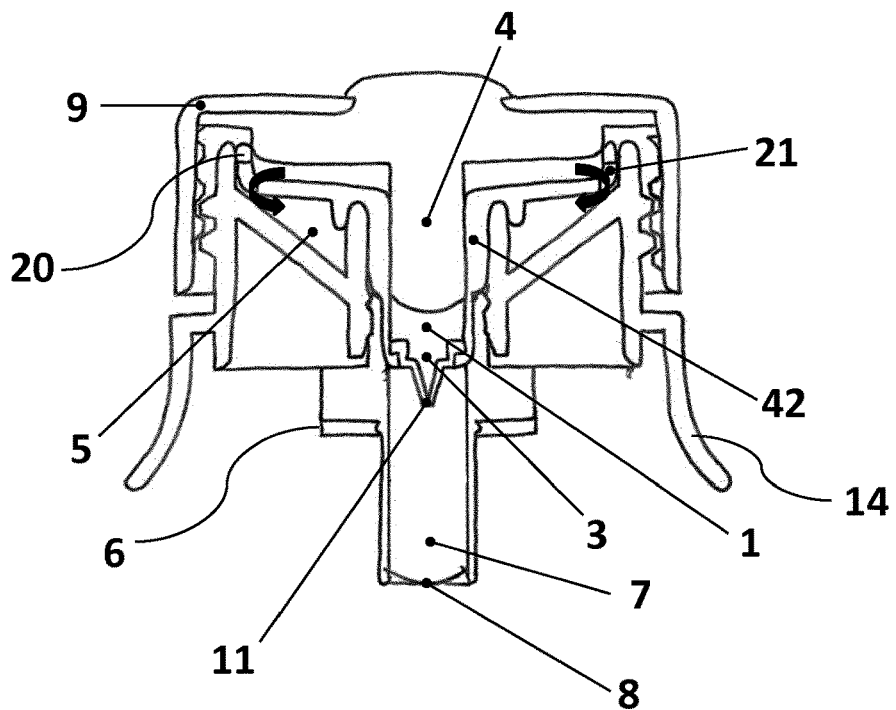
Figure 7C:
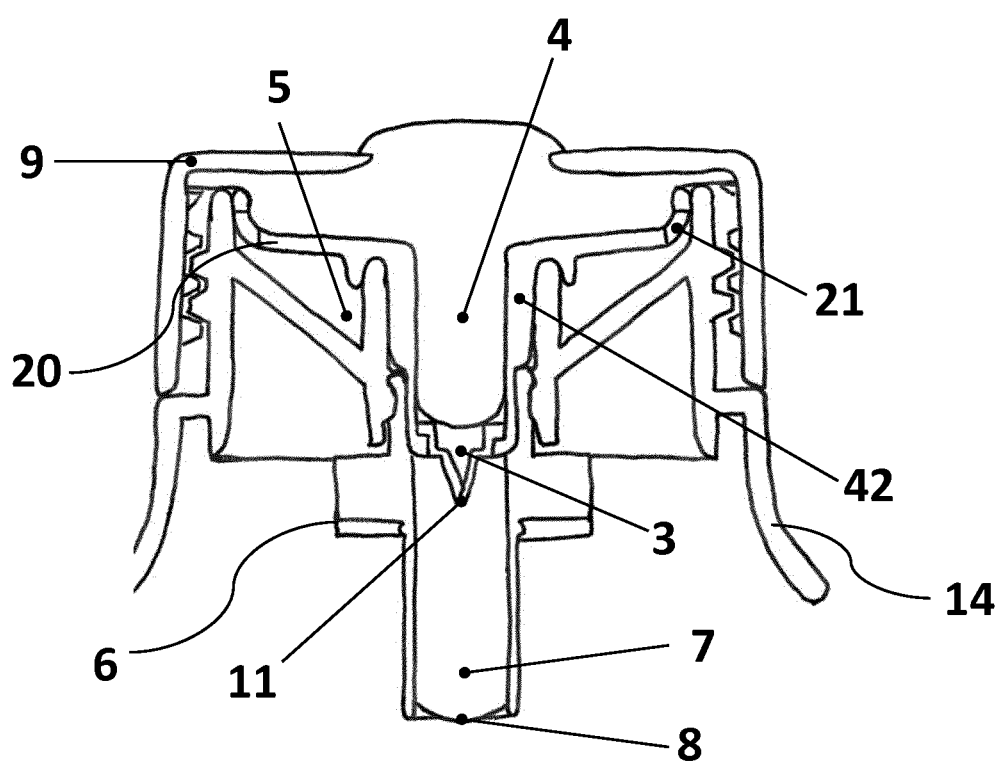

The lid (9) of the dosing system may be e.g. a hinged flip-top lid, a screw-on lid or a snap-on lid. Optionally, the lid is provided with a sealing lip. FIG. 6C shows a further embodiment with a screw-on lid, together with a funnel-shaped filling chamber (1), and a specifically shaped aerosol head component (14) which houses the overflow chamber (5). The dosing funnel (20) is placed into the aerosol head component (14) and the fill volume is poured into the cylindrical filling chamber (1) through the wide inlet opening (2). Overflow slits (21) are provided along the perimeter of the dosing funnel (20). Upon insertion of the cylindrical plunger (4) into the cylindrical part of the filling chamber (1), using the screw-on lid (9), the bottom end of the plunger (4) first forms a seal with the lateral wall (42) of the filling chamber (1) and starts to displace a metered volume of liquid, pushing it through the duckbill valve (11) of the outlet opening (3) into the nebulizer chamber (7). Due to the specific shape of the filling chamber (1), the risk of entrapping air in it upon insertion of the plunger (4) is greatly reduced. While the plunger (4) is inserted further towards its final position, the wider base of the plunger (4) forms a second seal with the lateral wall of the widened portion of the dosing funnel (20) at or near the inlet opening (2), just above the overflow slits (21), and depending on the fill volume pushes excess liquid through the overflow slits (21) into the overflow chamber (5), as indicated by the black arrows. The residual volume of non-metered liquid remaining in the filling chamber (1) after complete insertion of the plunger (4), as depicted in FIG. 7C, will again depend on the chosen dimensions and the volume of the plunger (4).

In a preferred embodiment, the funnel-shaped filling chamber (1) is attached to the aerosol head component (14) in order to not be lost or misplaced, e.g. by a flexible strap. In a further preferred embodiment, the funnel-shaped filling chamber (1) and the aerosol head component (14) are configured in such a way that the lid (9) can only be closed if the filling chamber (1) is positioned correctly, e.g. the thread of the screw-on lid catches only in a respective counter thread formed by the aerosol head component (14) and the correctly positioned filling chamber (1) together.

While in the above described embodiments the inlet opening (2) and the outlet opening (3) of the filling chamber (1) are typically separate, with the outlet opening (3) typically being positioned below the inlet opening (2) when in operational orientation, there may also be embodiments wherein the two openings are the same and/or wherein alternatively one opening includes the other.

Figure 8A:
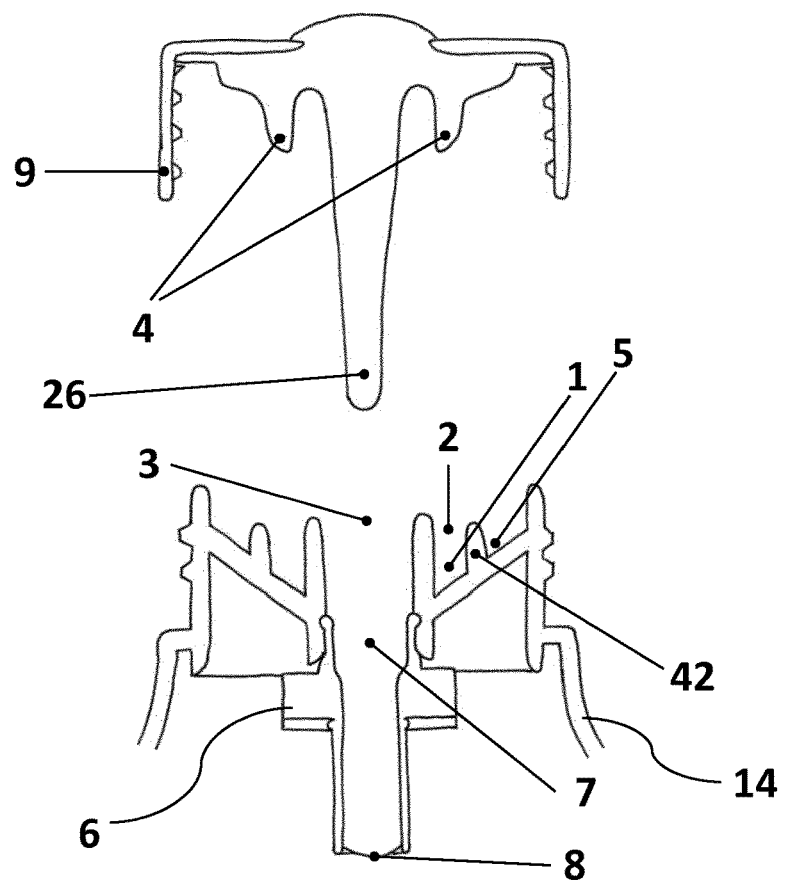
FIGS. 8A-B show a dosing system according to an embodiment of the invention in open state (A) and in closed state (B)

FIGS. 8A and B show an embodiment of the invention wherein the inlet opening (2) comprises the outlet opening (3) in such a way that the outlet opening (3) is radially surrounded by the inlet opening (2). It also represents an embodiment wherein the plunger (4) and the filling chamber (1) are not cylindrical but configured as matching ring-shaped forms; the plunger being the convex part (or curving out, or bulging outward, or protruding, or positive) and the filling chamber being the respective concave counter-part (or curving in, or bulging inwards, or negative).

Figure 8B:
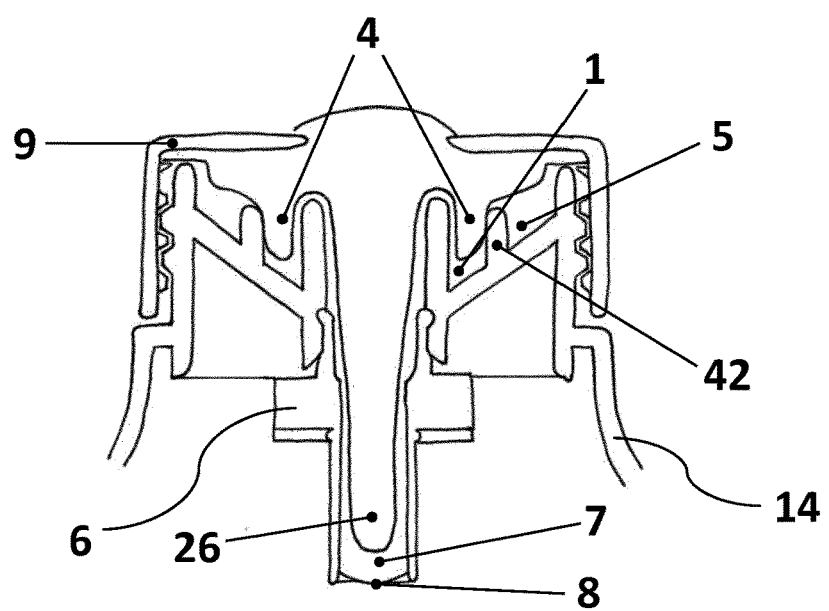

Prior to use of the inhalation device, the user would pour the pre-defined fill volume into the filling chamber (1), i.e. the inner of the two ring segments. Pouring liquid into the outlet opening (3) and thus the nebulizer chamber (7) should be avoided. Optionally, a filling aid may be provided which covers the outlet opening (3) and guides the pre-defined fill volume into the two outer ring segments filling chamber (1)

and which is then removed before mounting the screw-on lid (9). Depending on the volume of liquid filled into the device, some excess liquid may flow into the overflow chamber (5), i.e. the outer of the two ring segments. Since the outlet opening (3) in this embodiment is positioned above the maximum fill level of the filling chamber (1), no closing means are required to avoid filled liquid flowing out the outlet opening (3) by gravity. Only upon insertion of the plunger (4), a seal is formed (see seal 3 in FIG. 8B) between the lateral walls of the filling chamber (1) and the bottom end of the plunger (4), such that liquid displaced in the filling chamber (1) is pushed upwards. In effect, the metered volume flows into the nebulizer chamber (7).

The embodiment depicted in FIG. 8 further exhibits a safety plunger (26), which is does not determine the metered volume. Instead, it functions as a safety feature: in cases where the user accidentally fills the pre-defined fill volume into the nebulizer chamber (7) directly and closes the lid (9), the safety plunger (26) will push out most of it to avoid overdosing.

Figure 9:
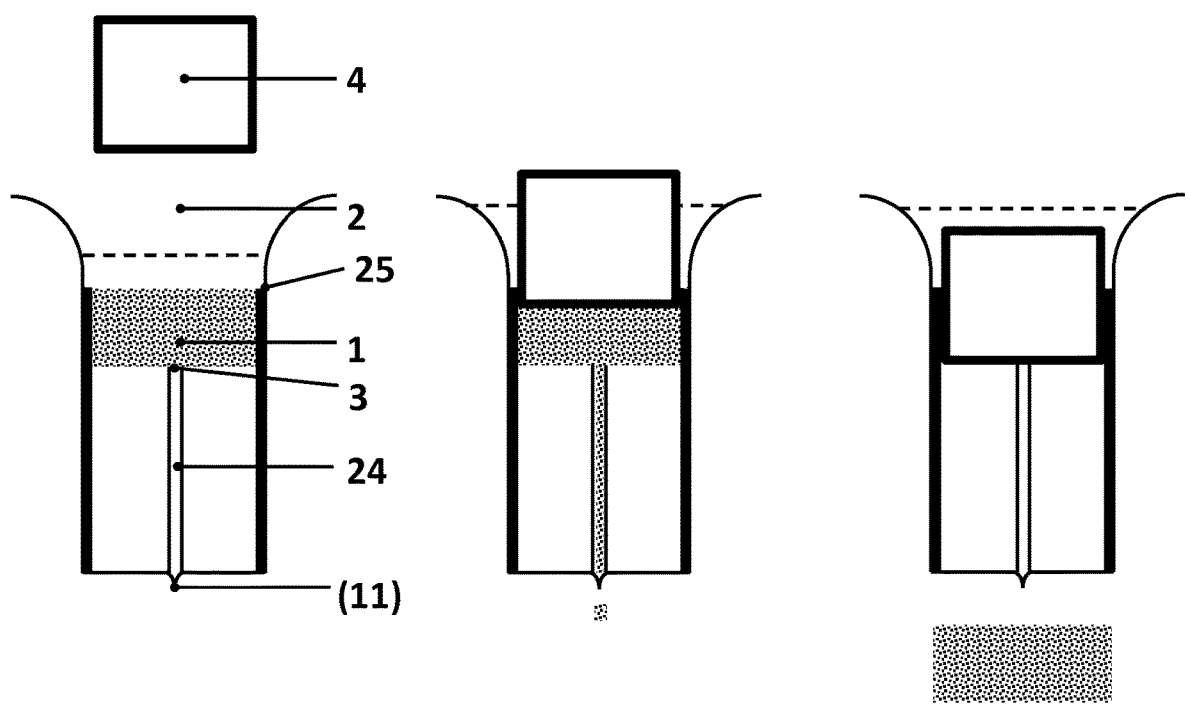
FIG. 9 shows a simplified display of a dosing system according to an embodiment of the invention; the dashed line marks the fill level of e.g. 1 ml poured in the fill chamber; the dotted area represents the volume to be dosed

FIG. 9 shows a simplified display of an alternative dosing system according to the invention without overflow chamber, but with a large residual space for excess liquid which is not to be nebulized. The system has a filling chamber (1) with an inlet opening (2) and a vertical pipe (24) positioned, approximately centered, at the bottom of the filling chamber (1). The vertical pipe may function as a capillary tube which closes the outlet opening (3) and keeps the liquid from flowing out of the filling chamber (1) by gravity. Alternatively, the pipe (24) may be wider and provided with a closing means, such as a duckbill valve (11) a liquid flow resistor, a nozzle, a valve, a one-way valve, a slit valve, a ball valve or the like.

Prior to use of the inhalation device, the fill volume is poured into the filling chamber (1); an exemplary fill level being indicated by the dashed line in FIG. 9. When inserting the plunger (4), the excess liquid above a sealing edge (25) is first displaced and rises around the plunger (4). The wall of the filling chamber (1) is shaped to accommodate this rising liquid level without any spills, even when the filling chamber (1) is slightly overfilled and/or if the user tilts the device slightly out of the operational orientation. Upon reaching the sealing edge (25), which marks the transition to a cylindric portion of the filling chamber (1), the plunger (4) seals and closes the filling chamber (1) and pushes the metered volume (as indicated by the dotted area in FIG. 9) through the outlet opening (3) and the pipe (24), (optionally through a closing means such as a duckbill-valve (11)) towards the nebulizing chamber (not shown in FIG. 9).

FIGS. 10A and B show an embodiment wherein the filling chamber (1) is housed in the screw-on lid (9), as a part of a separation chamber (28). The separation chamber (28) mainly comprises a flexible funnel-shaped filling chamber (1), e.g. made of silicone, with a slit valve (22) e.g. a cross-slit valve at its outlet opening (3). The widened upper section (29) of the filling chamber (1) is attached to a sealing lip (31) of the lid (9) via several (e.g. 3 to 8) thin, rigid funnel ribs (30) spaced around the upper perimeter of the filling chamber (1). When the lid is not fully screwed on the aerosol head component (14) yet, the funnel ribs are tilted sideways in such a way that the perimeter of the upper section (29) is held locked against the lid's sturdy central cylinder (34). This is to ensure that filled liquid does not spill from the filling chamber (1) during minor handling errors such as slight tilting of the dosing system.

Prior to use of the inhalation device, the lid (9) is positioned on the aerosol head component (14), but not screwed on yet, and the liquid is poured into the filling chamber (1) by inserting an opened cartridge, or vial, or ampoule (27) with the open end first into the lid's (9) cartridge port (32). A puncture pin (33) extending from the lid (9) causes the disruption of any surface tension of the liquid in the cartridge (27), such that the liquid will flow out freely through the inlet opening (2) into the filling chamber (1), where it is held back by the closed slit valve (22) at the outlet opening (3). An exemplary fill level is indicated by the dashed line in FIG. 10A. The filling chamber (1) rests on the central cylinder (35) of the aerosol head component (14), so that when the lid (9) is screwed on, it gradually gets pressed against the plunger (4) and the lid (9). Thereby, the plunger (4) is inserted into the filling chamber (1) and pushes the metered volume through the slit valve (22) at the outlet opening (3) into the nebulizer chamber (7). At the same time, the funnel ribs (34) recover from their tilted positions. As they straighten up, the perimeter of the widened upper section (29) is pressed downwards, away from the central cylinder of the lid (34) until it is inverted, or folded down, as shown in FIG. 10B. In this position, excess volume of liquid may flow from the inverted upper section (29) into the overflow chamber (5) housed in the aerosol head component (14). If the lid (9) is subsequently unscrewed, accidentally or after use, this excess liquid remains in the overflow chamber (5). Further excess liquid which is not pushed through the slit valve (22) may be held back in the filling chamber (1).

In summary, this means that in the above described embodiments, the plunger, while being at least partially inserted, sealingly contacts the lateral wall (42) of the filling chamber (1) to displace the metered volume into the nebulizer chamber (7) during further insertion until reaching its final position. Typically, this displacement into the nebulizer chamber (7) involves pushing the metered volume through a valve at the outlet opening (3). This means that the metered volume is actively separated from an excess by the movement of the plunger.

Alternative embodiments of the invention are shown now in FIGS. 11 to 14. Unlike the above described embodiments, the plunger in the embodiments in FIGS. 11 to 14 does not displace, or push, the metered volume to the nebulizer chamber (7) but merely isolates it from an excess of liquid (not to be dosed) once the plunger has reached its final position. This approach may be understood as a kind of "reverse dosing" in that an excess is actively separated from the metered volume by the movement of the plunger, rather than vice versa. Once isolated by the plunger in its final position, the metered volume is either allowed to simply flow freely, by gravity, into the nebulizer chamber (7) as depicted in FIGS. 12A and B; or the nebulizer chamber (7) itself forms the filling chamber (1a) from the metered volume may be nebulized directly, as depicted in FIGS. 11, 13A to E and 14A and B. This is explained in more detail below and with regard to the figures.

Figure 12A:
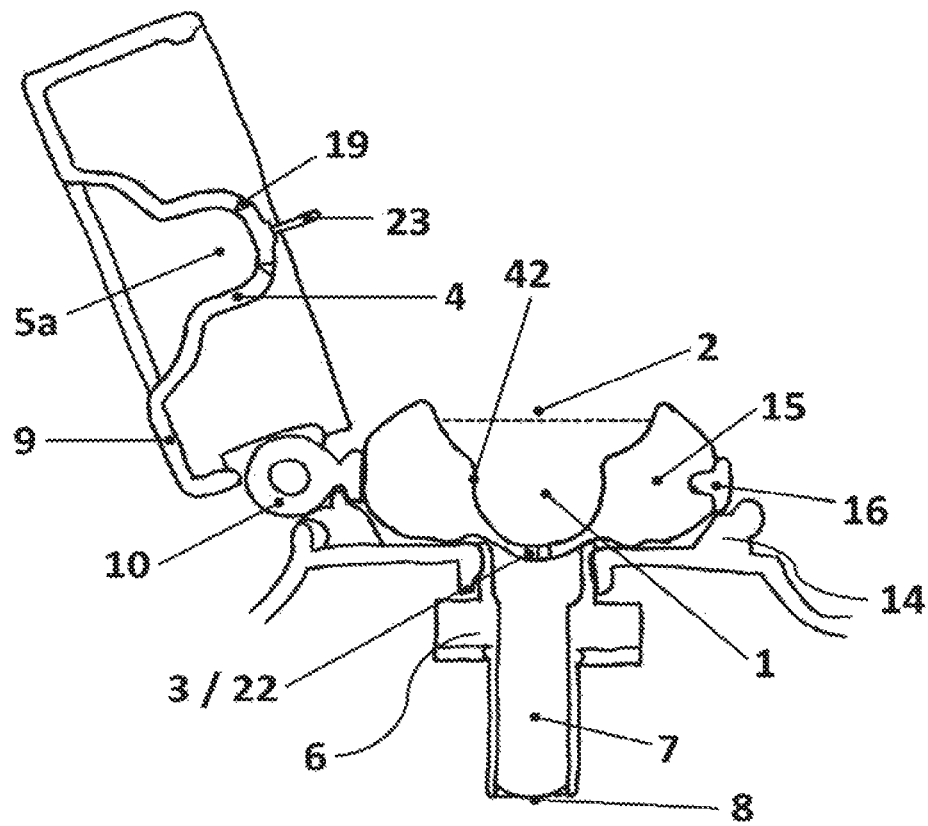
FIGS. 12A-B show a dosing system according to an embodiment of the invention in open state (A) and in closed state (B); dashed lines represent liquid levels.
Figure 12B:
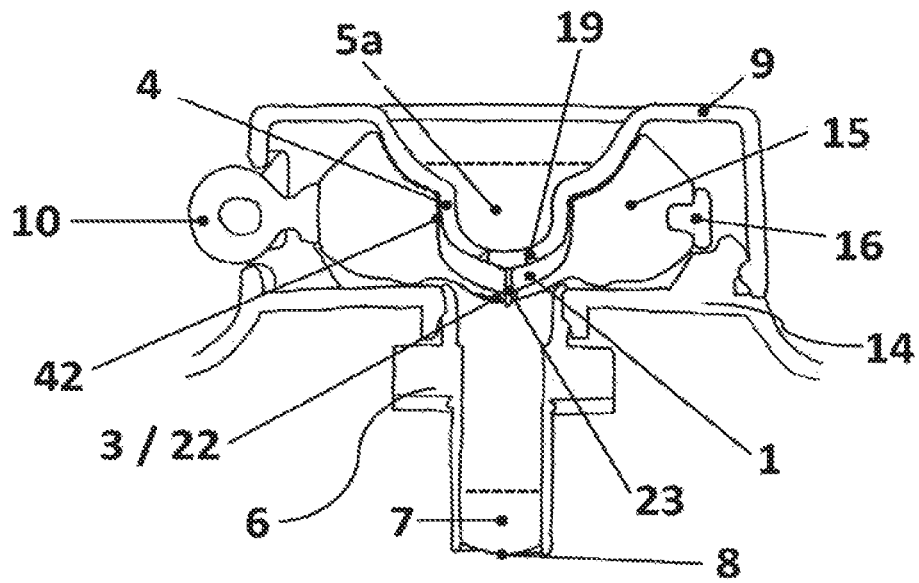

FIGS. 12A and B show another embodiment with an overflow chamber (5a) accommodated in the lid (9), and more specifically within a hollow plunger (4); i.e. the overflow chamber (5a) is associated with the plunger (4). Low resistance one-way valves (19) provided near the bottom end of the plunger (4) allow a unidirectional flow of excess liquid from the filling chamber (1) into the overflow chamber (5) under slight pressure, i.e. when the plunger (4) is at least partially inserted into the filling chamber (1a). When the plunger is fully inserted, (e.g. when the lid is fully closed), a sealing contact is formed between the plunger (4) and the lateral wall (42) of the filling chamber (1a) and excess volume and metered volume are separated. The metered volume then flows freely from the outlet opening (3) due to a release pin (23) opening the slit valve (22), which closed the outlet opening (3) until the plunger reached its final position. This release pin (23) is attached to, or an integral part of, the bottom end of the plunger (4), and its length is adjusted according to the volume to be metered as defined by the final position, or insertion depth, of the plunger (4). Thus, unlike in the embodiments described earlier, the metered volume is still controlled by the dimensions and/or insertion depth of the plunger (4) but it is transferred to the nebulizer chamber (7) by the action of the release pin (23), not by the plunger (4) pushing it out. It is actually the excess volume which is displaced here by the plunger (4), whereas the metered volume flows through the slit valve (22) when opened by the release pin (23).

The invention further provides a dosing system for an inhalation device, comprising:

(a) a nebulizer chamber (7);

(b) an aerosol head component (14);

(c) a filling chamber (1a) for receiving a liquid to be aerosolized, formed by the nebulizer chamber (7) and the aerosol head (14), the filling chamber (1a) having a lateral wall (42), an inlet opening (2) and an outlet opening (3) and a mesh (8) affixed to the outlet opening (3); and (d) a plunger (4) which is at least partially insertable into the filling chamber (1a), and which sealingly contacts the lateral wall (42) of the filling chamber (1a) upon being at least partially inserted into the filling chamber after the filling chamber has received at least a predefined fill volume of the liquid such as to isolate a metered volume of the liquid; wherein the metered volume is smaller than the fill volume.

Optionally, the inhalation device comprises a nebulizer. More specifically, the nebulizer may be a vibrating mesh nebulizer.

According to this aspect, the essential function of the plunger (4) is to isolate the metered volume from the non-metered portion of the fill volume by forming a seal with the lateral wall (42) of the filling chamber (1a) in the inserted state. The metered volume of liquid can then be nebulized directly or transferred to a nebulizing means (6).

Figure 11A:
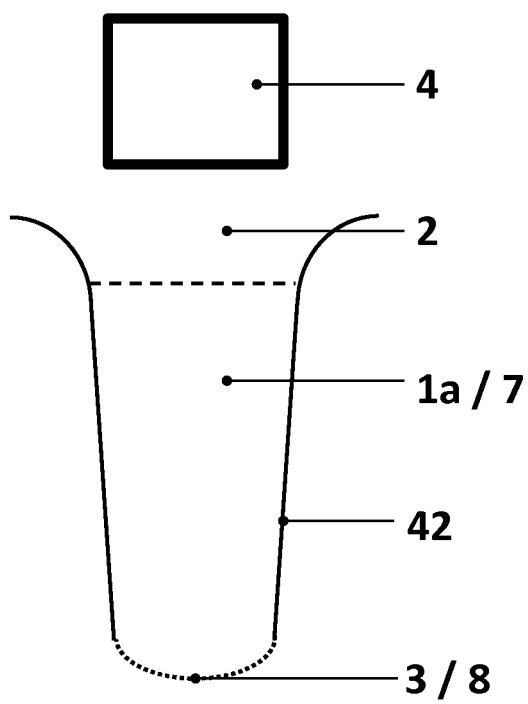
FIGS. 11A-B show a dosing system according to an embodiment of the invention in open state (A) and in closed state (B); dashed lines represent liquid levels
Figure 11B:
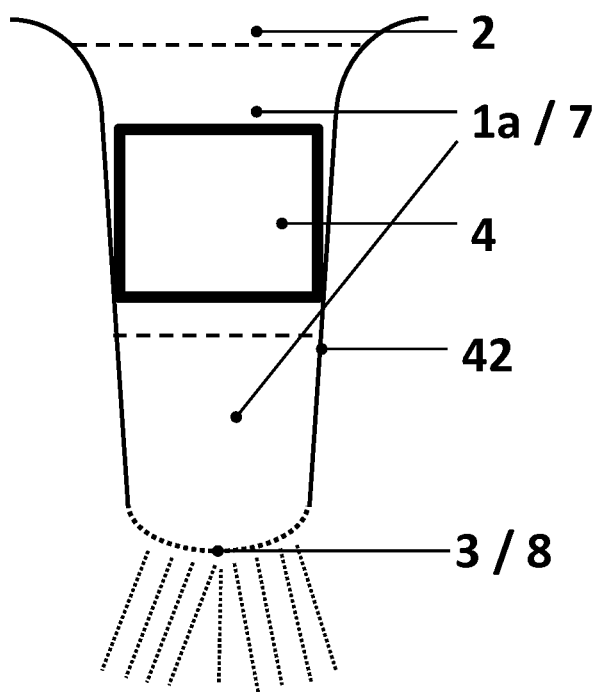

FIGS. 11A and B show a simplified representation of a dosing system according to this embodiment, with dashed lines representing exemplary liquid levels. The dosing system comprises a filling chamber (1a) with a slightly tapered lateral wall (42) and an inlet opening (2) through which the fill volume is received. The outlet opening (3) is closed by the mesh (8) of a vibrating mesh nebulizer; i.e. in this embodiment, the filling chamber (1a) and the nebulizer chamber (7) are identical. After the fill volume has been filled in, the plunger (4) is at least partially inserted (as shown in FIG. 11B), causing some excess liquid to rise around the plunger (4) until the sealing surface of the plunger (4; in FIG. 11B the bottom end of the plunger) sealingly contacts the lateral walls (42) of the filling chamber (1a), or nebulizer chamber (7). Thereby, the metered volume is isolated below the plunger (4) and can now gradually pass through the vibrating mesh (8) in the form of an aerosol, as indicated by the dotted lines below the mesh (8).

Typically, the simplified dosing system in FIGS. 11A and B further comprises an overflow chamber (5), which may be associated with the plunger (4), such as the overflow chamber (5a) depicted in FIGS. 13A to E and 14A and B.

Optionally, when in an operating orientation, the inlet opening (2) is located at an upper end of the filling chamber (1a) and the outlet opening is located at its lower end, so that the liquid to be aerosolized flows freely by gravity from the inlet opening (2) towards the outlet opening (3) when the filling chamber is filled. If a vibrating mesh nebulizer is used, the mesh (8) of the vibrating mesh nebulizer may be positioned at the outlet opening (3) and may have a horizontal orientation when in the operating mode.

Optionally, the filling chamber, or the portion of the filling chamber into which the plunger or the insertable portion of the plunger is inserted, and/or the plunger, or the portion of the plunger that is inserted into the filling chamber, is somewhat cylindrical, or substantially cylindrical.

Optionally, the filling chamber, or the portion of the filling chamber into which the plunger or the insertable portion of the plunger is inserted, and/or the plunger, or the portion of the plunger which is insertable into the filling chamber, may be made of a flexible material.

Optionally, the filling chamber is closable prior to and during operation of the inhalation device.

Optionally, the plunger is sized and shaped such as to be capable of closing the filling chamber; or the plunger is connectable to, or an integral part of, a lid which is capable of closing the filling chamber. In a more specific embodiment, the plunger is at least partially inserted into the filling chamber by closing the filling chamber.

In one embodiment, the plunger seals the filling chamber towards the inlet opening during its at least partial insertion into the filling chamber, such that no liquid leaves the filling chamber through the inlet opening.

In the embodiment shown in FIGS. 13A-E, a funnel-shaped filling chamber (1a) is formed by the nebulizer chamber (7) and the aerosol head component (14). The aerosol head component (14) is further equipped with a flexible gasket component (36), made e.g. from silicone. The gasket component comprises a sealing lip (31), a cylindrical plunger (4) with a central channel (39), an overflow chamber (5a), a one-way valve (38) and a gasket (37). An opened vial (27) or other container holding a liquid may be inserted into the gasket (37) head first, i.e. upside down. Surface tension or a slight underpressure may prevent the liquid to immediately empty into the filling chamber (1a). Exemplary liquid levels are shown as dashed lines in FIG. 13A. The central gasket opening (41) serves as the inlet opening (2) of the filling chamber (1a). A mesh (8) is affixed to the outlet opening (3).

Figure 13A:
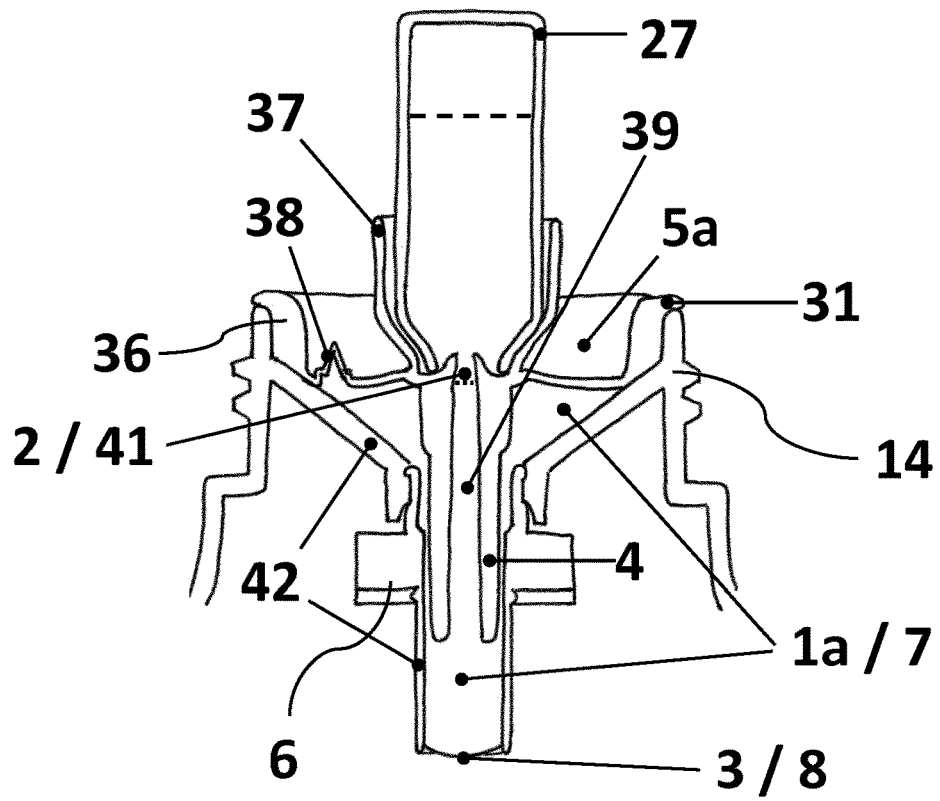
FIGS. 13A-E show a dosing system according to an embodiment of the invention in different steps of the filling procedure (A-C), in open state (D) and in closed state (E); dashed lines represent liquid levels
Figure 13B:
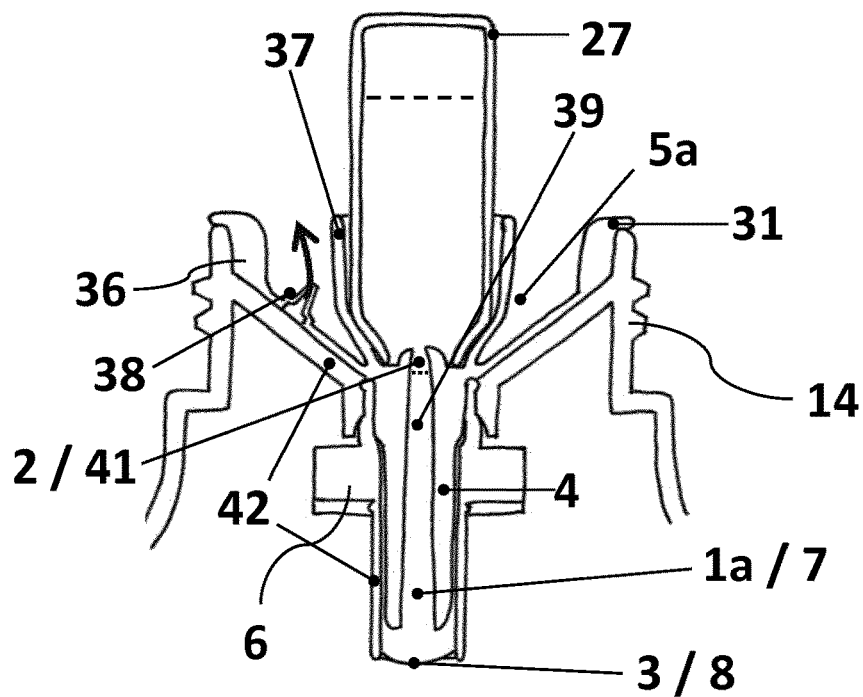
Figure 13C:
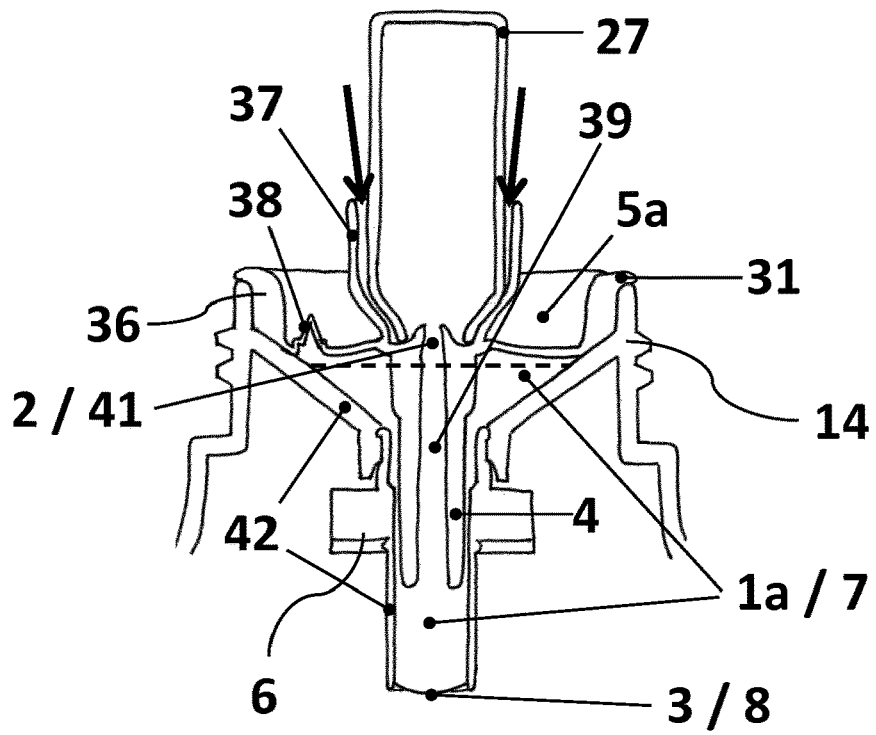

When the vial (27) is pressed down as shown in FIG. 13B, the gasket (37) forms a seal around it, and the air trapped between the aerosol head component (14) and the gasket component (36) escapes through a one-way valve (38), e.g. a duckbill valve, as indicated by the arrow in FIG. 13B. When releasing the pressure from the vial (27), the flexible gasket component (36) flips back into its original shape (as shown in FIG. 13C), thereby creating an underpressure sufficient to suck out the liquid from the vial (27). The liquid is conducted, through the channel (39) of the plunger (4) into the filling chamber (1a). At the same time, the seal between the gasket (37) and the vial (27) opens so that air can be drawn in (as indicated by the arrows in FIG. 13C) and the empty vial (27) can be removed from the gasket (37).

Figure 13D:
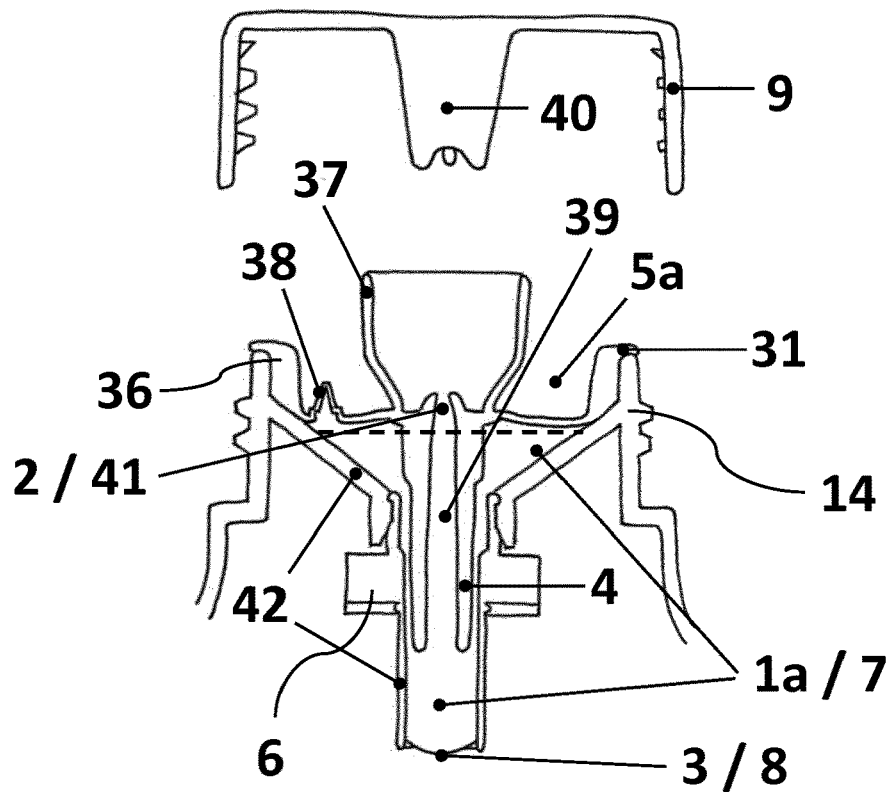
Figure 13E:
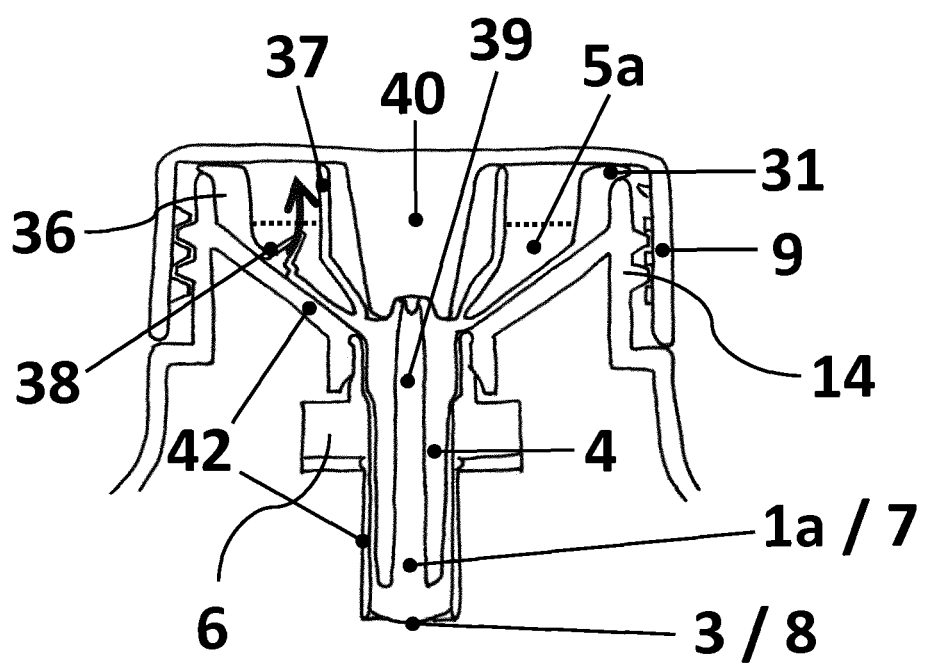

Subsequently, a lid (9) is screwed on to the aerosol head component (14), as shown in FIGS. 13D and E. The lid (9) comprises a central stopper (40) that is shaped and sized such as to match the gasket (37) and close the central gasket opening (41). By closing the lid (9), the flexible gasket component (36) and the plunger (4) attached to it are pressed down such that the gasket component (36) forms a funnel-shaped overflow chamber (5a) at the upper side of the gasket component (36), whereby air and excess liquid trapped between the aerosol head (14) and the lower side of the gasket component (36) are displaced and pushed through the one-way valve (38) into the overflow chamber (5a), as indicated by the arrow in FIG. 13E. The flow resistance of the mesh (8) is higher than that of the one-way valve (38) so that no liquid is pushed through the mesh (8) upon screwing on the lid (9).

Upon complete closure of the lid (9), the gasket component (36) is pressed against the aerosol head component (14), with the outer zone of the gasket component (36) forming a sealing lip (31) between the lid (9) and the aerosol head component (14). Thereby, the metered volume is isolated and separated from excess liquid which is pushed through the one-way valve (38) into the overflow chamber (5a). The metered volume remains in the lower part of the filling chamber (1a) which is formed by the nebulizer chamber (7), in the channel (39) in the plunger (4) and in the gap formed between the lateral wall (42) of the nebulizer chamber (7) and the plunger (4). Exemplary liquid levels are shown as dashed lines in FIG. 13E.

Figure 14A:
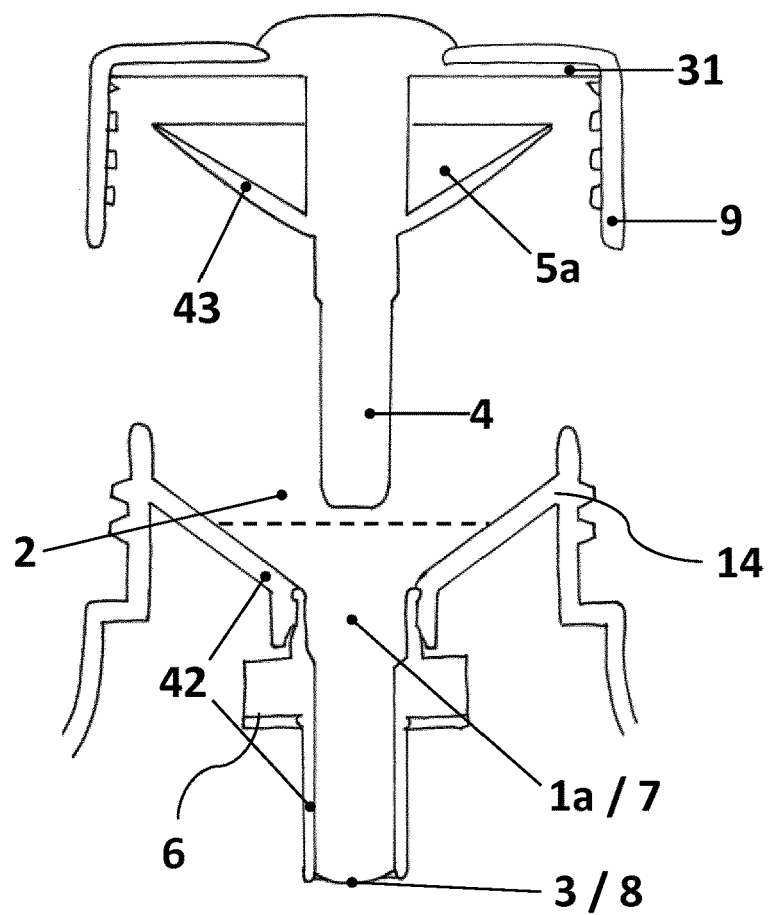
FIGS. 14A-B show a dosing system according to an embodiment of the invention in open state (A) and in closed state (B); dashed lines represent liquid levels.
Figure 14B:
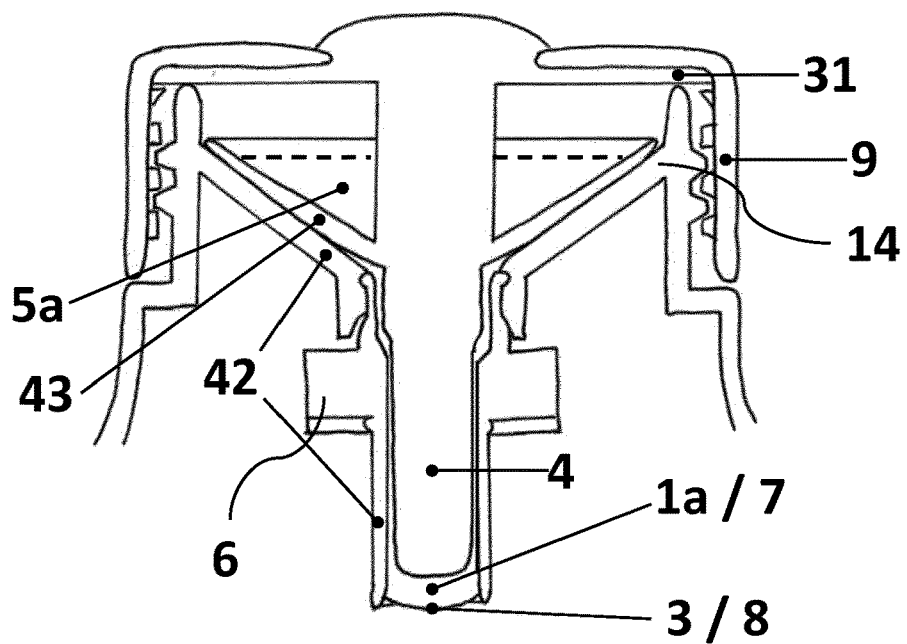

Another embodiment is shown in FIGS. 14A and B. The dosing system depicted comprises a funnel-shaped filling chamber (1a) for receiving a liquid to be aerosolized (an exemplary fill level indicated by a dashed line). The filling chamber (1a) has a lateral wall (42), an inlet opening (2) and an outlet opening (3) which is covered by the mesh (8) of a vibrating mesh nebulizing means (6). Due to the mesh (8), the liquid cannot flow through the outlet opening (3) by gravity. The funnel-shaped filling chamber (1a) is formed by the nebulizer chamber (7) and the aerosol head component (14).

The dosing system further comprises a plunger (4) which is at least partially insertable into the filling chamber (1a), and which is sized and configured such as to sealingly contact the lateral wall (42) of the filling chamber (1a) upon being at least partially inserted, such as to isolate a metered volume of the liquid which is smaller than the fill volume. The upper section of the plunger (4) further comprises, or is associated with, an overflow chamber (5a) which is shaped like a funnel or an inverted umbrella having a funnel wall (43). Once the filling chamber (1a) is filled with liquid, the plunger (4) is gradually inserted into the filling chamber (1a) by screwing on the lid (9). Some excess liquid may be displaced by the plunger (4) and pushed into the overflow chamber (5a); more specifically the plunger (4) and the funnel wall (43) displace the excess such that it overflows into the overflow chamber (5a). Upon complete closure of the lid (9), the sealing lip (31) forms a seal between the lid (9) and the aerosol head component (14) while the plunger (4) sealingly contacts the lateral walls (42) of the filling chamber (1a). More specifically, the funnel wall (43) associated with the plunger (4) forms a seal with the upper part of the filling chamber (1a) formed by the aerosol head component (14). Thus, the metered volume is separated from the non-metered portion of the liquid and ready for nebulization through the mesh (8).

Similar to the other embodiments, there may be provided a small opening for venting (not shown) in the lateral wall of the nebulizer chamber (7) to avoid underpressure when the metered dose of liquid is gradually removed by nebulization through the mesh (8). For the embodiments in FIGS. 13A to E and FIGS. 14A and B (where the nebulizer chamber (7) forms the filling chamber (1a) and will thus be filled initially with a volume larger than the metered one) such an opening has to be provided with a one-way valve such that none of the fill volume and/or metered volume is lost through said venting opening.

It should be noted that while FIGS. 14A and B depict a rather large plunger (4) which is intended for dosing very small volumes, this embodiment is also suitable for larger volumes in that the diameter and/or length of the plunger (4) can be reduced, such as to displace less excess from filling chamber (1a).

Optionally, the dosing system according to the invention and/or the inhalation device according to the invention are equipped with a sensor means which allows detecting when the filling chamber (1) is empty, such as to prompt the automatic switching off of the nebulizing means. Optionally, the inhalation device may further comprise a signaling means (or feedback means) in order to provide specific information to the user, such as that the aerosolization of the metered volume is completed.

Once the aerosolization is completed, the lid (9) may be removed, excess liquid may be discarded and the dosing system rinsed out with water.

The inventors have found that the dosing system according to the invention allows precise, accurate and reproducible dosing, even in cases when the metered volume is substantially smaller than the fill volume, or the pre-defined, or minimal, fill volume. In some embodiments, the metered volume is not more than 90% of the pre-defined fill volume. Optionally, the metered volume is not more than 80% of the pre-defined fill volume. In other cases, the metered volume is not more than 70%, 60%, or 50% of the pre-filled fill volume. For example, the metered volume ranges from e.g. 10% up to 90%, or from 20% to 80%, of the pre-defined fill volume.

The metered volume is typically not more than about 5 ml. In many cases, it is not more than about 3 ml, or not more than about 2 ml, or not more than about 1 ml, respectively. Optionally, the metered volume may also be not more than about 0.5 ml, or not more than about 0.4 ml, or even not more than about 0.3 ml.

The residual volume of liquid in the dosing system, i.e. the volume which is not metered and fed to the nebulizing means, is typically at least about 10 µl. Optionally, the residual volume is at least about 20 µl, or 30 µl, or 50 µl, or 100 µl, or 200 µl, or 300 µl, or 500 µl, or 1 ml, or 2 ml, or 3 ml, respectively.

In another embodiment, the invention comprises a dosing system for an inhalation device, comprising
  (a) a filling chamber for receiving a liquid to be aerosolized, the filling chamber having an inlet opening and an outlet opening which is closable at least to the extent as to prevent the liquid received by the filling chamber from flowing through the outlet opening by gravity; and
  (b) a plunger which is at least partially insertable into the filling chamber, and which is sized and configured such as to push, while being at least partially inserted into the filling chamber after the filling chamber has received at least a pre-defined fill volume of the liquid, a metered volume of the liquid out from the filling chamber through the outlet opening, wherein the metered volume is smaller than the fill volume.

In another embodiment, the invention provides a dosing system for an inhalation device, comprising:
  (a) a filling chamber for receiving a liquid to be aerosolized, the filling chamber having a lateral wall, an inlet opening and an outlet opening which is configured so as to and/or closable at least to the extent as to prevent the liquid received by the filling chamber from flowing through the outlet opening by gravity; and
  (b) a plunger which is at least partially insertable into the filling chamber, and which is sized and configured such as to sealingly contact the lateral wall of the filling chamber upon being at least partially inserted into the filling chamber after the filling chamber has received at least a predefined fill volume of the liquid such as to isolate a metered volume of the liquid; wherein the metered volume is smaller than the fill volume. The invention further provides a method for dosing a liquid to be aerosolized comprising the steps of:

(1) providing a filling chamber for receiving a liquid to be aerosolized, the filling chamber having (a) an inlet opening and (b) an outlet opening which is closable at least to the extent such as to prevent the liquid received by the filling chamber from flowing through the outlet opening by gravity; and (2) providing a plunger which is at least partially insertable into the filling chamber, and which is sized and configured such as to push, while being at least partially inserted into the filling chamber after the filling chamber has received at least a predefined fill volume of the liquid, a metered volume of the liquid out from the filling chamber through the outlet opening; and (3) filling the filling chamber with at least a predefined fill volume of the liquid; and (4) at least partially inserting the plunger such as to push a metered volume of the liquid out from the filling chamber through the outlet opening, wherein the metered volume is smaller than the fill volume.

While some specific embodiments have been described in detail and have been shown in figures, it is to be understood that the invention is not limited to the specific embodiments in the description or in the figures alone. Other advantageous combinations of all disclosed features are feasible and fall under the scope of this invention.

The invention claimed is:

1. A dosing system for an inhalation device, comprising
   (a) a filling chamber for receiving a liquid to be aerosolized, the filling chamber having
      a lateral wall with an outer side,
      an inlet opening, and
      an outlet opening with a closing means for closing the outlet opening;
   (b) an overflow chamber surrounding the filling chamber for isolating any excess volume of liquid which is not supposed to be administered to the user so that it cannot be re-dosed accidentally, the overflow chamber comprising a cavity and having an outer wall with an inner side facing said cavity, wherein the outer side of the lateral wall of the filling chamber faces the cavity of the overflow chamber; and
   (c) a plunger which is at least partially insertable into the filling chamber, and which is configured to sealingly contact the lateral wall when being at least partially inserted into the filling chamber and configured to push, after the filling chamber has received at least a predefined fill volume of the liquid, a metered volume of the liquid out from the filling chamber through the outlet opening, wherein the metered volume is smaller than the predefined fill volume,
   wherein the filling chamber has a portion into which the plunger is capable of being inserted and wherein the portion of the filling chamber into which the plunger is capable of being inserted is made of a flexible material,
   wherein the dosing system comprises a flip-top lid which is attached with an off-centered hinge,
   wherein the plunger is connectable to, or an integral part of the flip-top lid,
   wherein the plunger is sized and shaped such as to be capable of closing the filling chamber, or wherein the lid is capable of closing the filling chamber, and
   wherein the dosing system has an operating orientation, wherein the filling chamber has an upper end and a lower end, and wherein, in the operating orientation, the inlet opening is located at the upper end of the filling chamber, and the outlet opening is located at the lower end of the filling chamber.

2. An inhalation device comprising the dosing system according to claim 1 and a nebulizer selected from the group consisting of an ultrasonic nebulizer, a jet nebulizer, and a vibrating mesh nebulizer.

3. The dosing system according to claim 1, wherein the closing means is selected from the group consisting of a capillary tube, a liquid flow resistor, a nozzle, a valve, a one-way valve, a duckbill valve, a slit valve and a ball valve.

4. The inhalation device according to claim 2, wherein the inhalation device has an operating orientation, wherein the nebulizer is a vibrating mesh nebulizer, and wherein, in the operating orientation, the mesh of the vibrating mesh nebulizer is positioned below the outlet opening and has a horizontal orientation relative to an axis of the outlet opening.

5. The dosing system according to claim 1, wherein the plunger has a portion which is insertable into the filling chamber; and
   wherein the filling chamber, or the portion of the filling chamber into which the plunger or the insertable portion of the plunger is capable of being inserted and
   the plunger, or the portion of the plunger which is insertable into the filling chamber, are substantially cylindrical.

6. The dosing system according to claim 1, further comprising a residual pocket surrounding the outlet opening.

7. The dosing system for an inhalation device according to claim 1, wherein
   (a) the lateral wall has an upper end, and wherein the upper end of the lateral wall forms a bulge, and/or
   (b) the outer wall has an upper end, and wherein the upper end of the outer wall forms a bulge.

8. The dosing system according to claim 1, wherein the outer side and/or the inner side is concavely curved or leaning towards the overflow chamber.

9. A dosing system for an inhalation device, comprising
   (a) a filling chamber for receiving a liquid to be aerosolized, the filling chamber having
      a lateral wall with an outer side,
      an inlet opening, and
      an outlet opening with a closing means for closing the outlet opening;
   (b) an overflow chamber surrounding the filling chamber for isolating any excess volume of liquid which is not supposed to be administered to the user so that it cannot be re-dosed accidentally, the overflow chamber comprising a cavity and having an outer wall with an inner side facing said cavity, wherein the outer side of the lateral wall of the filling chamber faces the cavity of the overflow chamber; and
   (c) a plunger which is at least partially insertable into the filling chamber, and which is configured to sealingly contact the lateral wall when being at least partially inserted into the filling chamber and configured to push, after the filling chamber has received at least a predefined fill volume of the liquid, a metered volume of the liquid out from the filling chamber through the outlet opening, wherein the metered volume is smaller than the predefined fill volume, wherein the filling chamber has a portion into which the plunger is capable of being inserted and wherein the portion of the filling chamber into which the plunger is capable of being inserted is made of a flexible material, wherein the dosing system comprises a flip-top lid which is attached with an off-centered hinge, wherein the plunger is connectable to, or an integral part of the flip-top lid, wherein the plunger is sized and shaped such as to be capable of closing the filling chamber, or wherein the lid is capable of closing the filling chamber, and wherein the plunger is at least partially inserted into the filling chamber when the lid is in a closed position, and wherein when it is at least partially inserted into the filling chamber, the plunger is capable of sealing the filling chamber towards the inlet opening such that no liquid can leave the filling chamber through the inlet opening.

10. A method for dosing a liquid to be aerosolized comprising the steps of:

(1) providing a dosing system according to claim 1;

(2) filling the filling chamber with at least a predefined fill volume of the liquid; and (3) at least partially inserting the plunger such as to push a metered volume of the liquid out from the filling chamber through the outlet opening, wherein the metered volume is smaller than the fill volume.

* * * * *